US008211830B2

(12) United States Patent
Bailey et al.

(10) Patent No.: US 8,211,830 B2
(45) Date of Patent: Jul. 3, 2012

(54) FUNGAL ISOLATES AND BIOLOGICAL CONTROL COMPOSITIONS FOR THE CONTROL OF WEEDS

(75) Inventors: Karen L. Bailey, Saskatoon (CA); JoAnne Derby, Saskatoon (CA)

(73) Assignee: Her Majesty the Queen in Right of Canada, as represented by the Minister of Agriculture and Agri-Food Canada, Saskatoon (CA)

( * ) Notice: Subject to any disclaimer, the term of this patent is extended or adjusted under 35 U.S.C. 154(b) by 1253 days.

(21) Appl. No.: 10/478,829

(22) PCT Filed: May 30, 2002

(86) PCT No.: PCT/CA02/00797
§ 371 (c)(1), (2), (4) Date: Apr. 9, 2004

(87) PCT Pub. No.: WO02/96204
PCT Pub. Date: May 12, 2002

(65) Prior Publication Data

US 2005/0079978 A1 Apr. 14, 2005

Related U.S. Application Data

(60) Provisional application No. 60/294,475, filed on May 30, 2001.

(51) Int. Cl.

| | |
|---|---|
| ***A01N 63/00*** | (2006.01) |
| *A01N 25/26* | (2006.01) |
| *A01N 59/04* | (2006.01) |
| *A01N 25/00* | (2006.01) |
| *C12N 1/00* | (2006.01) |

(52) U.S. Cl. ........ 504/117; 504/100; 504/101; 504/116; 435/254.1; 530/823

(58) Field of Classification Search .................. 504/117, 504/100, 101, 116; 435/254.1, 911, 254/1; 530/823
See application file for complete search history.

(56) References Cited

U.S. PATENT DOCUMENTS 4,606,751 A 8/1986 Van Dyke et al.
(Continued)

FOREIGN PATENT DOCUMENTS

EP 0 187 341 7/1986
(Continued)

OTHER PUBLICATIONS

Graupner et al., 2003, *J. Nat. Prod.* 66: 1558-1561, "The Macrocidins: Novel Cyclic Tetramic Acids with Herbicidal Activity Produced by Phoma macrostoma".

(Continued)

*Primary Examiner* — Johann Richter
*Assistant Examiner* — Jane C Oswecki
(74) *Attorney, Agent, or Firm* — Merchant & Gould P.C.

(57) ABSTRACT

The present invention discloses fungal isolates of *Phoma* spp. or extracts obtained therefrom, useful for the control of broad leaf weeds, including Canada thistle, perennial sowthistle, dandelion, scentless chamomile, false cleavers, chickweed, wild buckwheat, and field bindweed. Te present invention also discloses biological control compositions comprising fungal isolates formulated in a growth medium for maintaining the viability of the fungal isolates when the biological control composition is applies to soil.

69 Claims, 5 Drawing Sheets

U.S. PATENT DOCUMENTS

| | | | | |
|---|---|---|---|---|
| 4,636,386 | A | 1/1987 | Anderson et al. | |
| 5,082,489 | A * | 1/1992 | Watson et al. | 504/117 |
| 5,391,538 | A * | 2/1995 | Heiny et al. | 504/117 |
| 5,472,690 | A | 12/1995 | Winder | |
| 5,635,444 | A | 6/1997 | Walker et al. | |
| 5,698,491 | A | 12/1997 | Kadir et al. | |
| 5,747,029 | A | 5/1998 | Walker et al. | |
| 5,795,845 | A | 8/1998 | Yang et al. | |
| 5,952,264 | A | 9/1999 | Walker et al. | |
| 5,993,802 | A | 11/1999 | Mallett | |
| 6,008,159 | A | 12/1999 | Medd et al. | |
| 6,403,530 | B1 * | 6/2002 | Sands et al. | 504/116.1 |
| 6,667,169 | B2 * | 12/2003 | Yaver et al. | 435/196 |
| 2006/0084574 | A1 * | 4/2006 | Bailey et al. | 504/117 |

FOREIGN PATENT DOCUMENTS

| | | | |
|---|---|---|---|
| EP | 0 497 728 | | 8/1992 |
| JP | 61-209507 | | 9/1986 |
| JP | 61-210006 | | 9/1986 |
| JP | 61210006 | * | 9/1986 |
| JP | 04-312508 | | 11/1992 |
| JP | 2001-000012 | | 1/2001 |
| WO | 98/08389 | | 3/1998 |
| WO | WO 00/54568 | | 9/2000 |
| WO | WO 02/096204 A1 | | 12/2002 |

OTHER PUBLICATIONS

Kothera et al., 2003, *Mycol. Res.*107: 297-304, “AFLP analysis of a worldwide collection of *Didymella bryoniae*”.

Larsen et al., 2002, *Plant Disease* 86: 928-932, “A Rapid Method Using PCR-Based SCAR Markers for the Detection and Identification of Phoma sclerotioides: The Cause of Brown Root Rot Disease of Alfalfa”.

Voight et al., 1998, *J. Phytopathology* 146: 567-576, “RAPD-based Molecular Probes for the Blackleg Fungus *Leptosphaeria maculans* (Phoma lingam): Evidence for Pathogenicity Group-specific Sequences in the Fungal Genomes”.

Vos et al., 1995, *Nucleic Acids Research* 23, “AFLP: a new technique for DNA fingerprinting”.

Zhou et al., 2005, *Mycologia* 97, “Molecular and genetic analyses of geographic variation in isolates of Phoma macrostoma used for biological weed control”.

Zhou et al., 2004, *Biological Control* 30, “Plant colonization and environmental fate of the biocontrol fungus Phoma macrostoma”.

Office Action for corresponding Mexican application 2008/001233 and English translation.

Office Action for corresponding Canadian application 2,448,890 mailed on Jul. 10, 2009.

“An Improved Invert Emulsion with High Water Retention for Mycoherbicide Delivery”, Connick et al., Weed Technology, 1991, vol. 5:442-444.

Office Action mailed on Feb. 2, 2009 for Co-pending U.S. Appl. No. 11/190,078, filed Jul. 25, 2005.

Notification of Reason for Refusal for corresponding Japanese application 2002-592726, dispatched on Feb. 3, 2009 (and English translation).

Connick, Jr. et al., “Application Note, Shelf life of a bioherbicide product,” *American Biotechnology Laboratory*, pp. 34-35 (Sep. 1996).

“Phytotoxic Metabolites of *Phoma Sorghina*, A New Foliar Pathogen of Pokeweed”, P. Venkatasubbaiah et al., Mycologia, 84(5), 1992, pp. 715-723.

First Report of the Teleomorph of an *Oidium* sp. Causing Powdery Mildew on Flowering Dogwood in South Carolina, M.R. Williamson et al., Agriculture and Natural Resources, Clemson University, Clemson SC 29634. Plant Dis. 83:200, 1999; published on-line as D-1998-1203-01N, 1998.

“Putaminoxin, A Phytotoxic Nonenolide From Phoma Putaminum” Evidente et al., Photochemistry, vol. 40, No. 6, pp. 1637-1641. 1995.

“Phoma Metabolites Toxic to Convolvulus spp.” M. Chrysayi-Tokousbalides, Phytopath., Medit., 1997, 36, 19-23.

“Laboratory Evaluation of Indigenous North American Fungi for Biological Control of Purple Loosestrife” Robert F. Nyvall et al., Biological Control 8, 37-42 (1997), Article No. BC960482.

Office Action for corresponding Australian Patent No. 2002311116 dated Oct. 6, 2006.

Office Action for corresponding Australian Patent No. 2002311116 dated Oct. 3, 2007.

Office Action for corresponding Canadian Application No. 2,448,890 dated Oct. 9, 2008.

Office Action for corresponding Chinese Application No. 200680034970.7 dated Oct. 9, 2010.

Office Action for corresponding European Application No. 02734935.6 dated Feb. 20, 2007.

Office Action for corresponding European Application No. 02734935.6 dated Mar. 25, 2008.

Summons to Attend Oral Proceedings for corresponding European Application No. 02734935.6 dated Mar. 10, 2009.

Extended European Search Report for corresponding European Application No. 06761182.2 dated Jul. 6, 2010.

Office Action for corresponding Japanese Application No. 2002-592726 dated Apr. 9, 2010.

Office Action for corresponding Mexican Application No. MX/a/2008/001233 dated Aug. 18, 2009.

Office Action for corresponding Mexican Application No. MX/a/2008/001233 dated Feb. 3, 2010.

Office Action for corresponding Mexican Application No. MX/a/2008/001233 dated May 7, 2010.

Office Action for corresponding Mexican Application No. PA/a/2003/010896 dated Dec. 7, 2005.

Office Action for corresponding Mexican Application No. PA/a/2003/010896 dated Dec. 11, 2009.

Office Action for corresponding Mexican Application No. PA/a/2003/010896 dated Mar. 1, 2010.

Office Action for corresponding New Zealand Patent No. 529796 dated Apr. 11, 2005.

Office Action for corresponding U.S. Appl. No. 11/190,078 dated Jun. 18, 2008.

Office Action for corresponding U.S. Appl. No. 11/190,078 dated Feb. 2, 2009.

Office Action for corresponding U.S. Appl. No. 11/190,078 dated Aug. 19, 2009.

International Search Report and Written Opinion for corresponding PCT Application PCT/CA2006/001223 dated Nov. 21, 2006.

International Preliminary Report on Patentability for corresponding PCT Application PCT/CA2006/001223 dated Dec. 10, 2007.

Agrios, “Plant Pathology”, 2nd Edition, 1978, pp. 30-31, 90-93.

Gilbert et al., “Phylogenetic signal in plant pathogen-host range”, PNAS, Mar. 20, 2007, vol. 104, No. 12, 4979-4983.

Melzer et al., “Index of Plant Hosts of *Sclerotinia minor*,” Canadian Journal of Plant Pathology, 19:272-280, 1997.

U.S. Department of Agriculture, Agricultural Research Service webpage on Phoma Proboscis, http://nt.ars.grin.gov/fungaldatabases/fungushost/new_hostFamGen.cfm, printed Sep. 4, 2007.

Wapshere, “A strategy for evaluating the safety of organisms for biological weed control,” Ann. Appl. Biol. (1974), 77, 201-211.

* cited by examiner

FUNGAL ISOLATES AND BIOLOGICAL CONTROL COMPOSITIONS FOR THE CONTROL OF WEEDS

This application claims priority to PCT/CA02/00797, filed May 30, 2002, which claims benefit to U.S. provisional application 60/294,475, filed May 30, 2001.

The present invention relates to bioherbicides. More specifically, the present invention relates to fungal bioherbicides and compositions comprising fungal bioherbicides.

BACKGROUND OF THE INVENTION

The use of pesticides to kill insects, weeds and other disease pests is common in agriculture. It has been estimated that Canadian farmers spend more than $750 million on pesticides, and U.S. and European estimates are likely to be several fold higher. On the Canadian prairies, 95% of the land seeded to wheat, barley, canola and flax is treated with one or more pesticides. However, despite extensive pesticide use, weeds continue to cause an estimated one billion dollars in crop losses in Canada alone every year.

Weeds are detrimental to agricultural crops because they are capable of outcompeting crop plants for space, sun and nutrients. Particularly troublesome weeds include Canada thistle (*Cirsium arvense*) and other members of the Aster family such as perennial sowthistle (*Sonchus arvense*), and dandelion (*Taraxacum officinale*).

Canada thistle (*Cirsium arvense* [L.] Scop.) is an aggressive perennial weed in field crops, pastures and roadsides, and is particularly prevalent in Western Canada where it occurs in about 50% of all fields. Canada thistle causes crop yield losses of about 15 to 60% in cereal, oilseed and pulse crops, depending on weed density. In cereal crops, densities of 6 to 20 Canada thistle plants per square meter result in an 18 to 30% loss in grain yield. In 1937, Canada thistle was designated. as a noxious weed by the Canadian Federal Seeds Act.

Although weeds of the Aster family, for example Canada thistle and dandelion, can reproduce by flowering, they are difficult to eradicate because their extensive root system. The roots are quite brittle and fragment easily during tillage. This results in greater shoot emergence from stimulated buds. Further adding to the difficulties of control, the root fragments carry sufficient food reserves to survive long periods under adverse conditions.

Control of Canada thistle in field crops is currently achieved by pre-seeding, in-crop, and post-harvest chemical control with herbicides, applied at sufficient rates to suppress top growth, or kill the roots. For example, Glyphosate is used as a pre-seeding treatment to kill Canada thistle, or used in-crop on glyphosate tolerant crops. Clopyralid is used for in-crop control to achieve the same effect but has problems with residual activity for some crops in the following year. Other product combinations only provide top growth suppression such as thifensulfuron and tribenuron-methyl or fenoxy-prop and MCPA. Other control options include growing competitive crops and seeding early to get vigorous crop growth before Canada thistle emergence and shallow tilling of soil to reduce root fragmentation and new shoot growth. Also, mowing may be used to control weeds on roadsides, ditches, headlands and fence lines. Controlling patches instead of entire fields is often recommended to reduce costs.

There are a number of drawbacks associated with non-chemical control of Canada thistle in addition to those discussed above. First, there are very few crops which are able to outcompete weeds such as Canada thistle and many crops cannot be seeded early enough to provide the crop with a competitive advantage to Canada thistle. Further, seeding crops earlier than usual may be an inconvenience to farmers. Also, shallow tillage of soil and mowing weeds to kill weeds or prevent weed flowering are only temporary solutions and are at best marginally effective in controlling weeds such as Canada thistle.

There are also several drawbacks associated with the use of chemical herbicides to control weeds such as Canada thistle. Herbicides are expensive and may be too expensive to be used by some farmers. Further, if a farmer uses less than the required dosage of herbicide to kill the weeds, there is an increased risk that some weeds may develop herbicide resistance. There is also an increased risk of herbicide resistance due to overuse of a herbicide. In addition, herbicides are not available for all crops and all situations. For example, there are no effective herbicides available for crops such as peas and lentil whereas some in-crop chemical herbicides only suppress top growth of weeds without controlling root growth, which is a short-term strategy often used for crops such as wheat, barley and canola. Residual herbicidal activity may also limit crop rotation for some crops and some agronomic herbicide practices may increase weed densities. There are also concerns about the short and long term safety of herbicides, both to consumers and the environment.

Environmental issues in the agri-food industry have become a priority with federal and provincial governments, including the development of alternatives for chemical pest control products, with the ultimate goal of reducing chemical pesticide use. Rising economic, environmental and social costs associated with agricultural inputs, spray drift, pesticide residues, government legislation for reduced pesticide use, along with the development of herbicide resistance in weeds make biological control agents attractive strategies for weed control for both agricultural and domestic use.

Broad-leaved weeds in turf situations, such as lawns, parks, and golf courses, disrupt the desired visual uniformity (i.e. are unsightly), create problems in the maintenance of the turf due to clumping and growth habits of the weeds, compete with the turf for light, nutrients, and water. Weeds are also are irritants to humans when allergic reactions to their pollen or the chemicals applied for weed control occur. Important weeds in turfgrass belong to the Compositae (such as dandelion, sowthistle), Caryophyllaceae (such as chickweed), and Rubiaceae, and Convolvulaceae. Typically, control of weeds in turf has been with selective, nonselective, systemic, and contact herbicides applied at various times (pre-plant, pre-emergence, and post-emergence). Public pressure is mounting to prevent the use of chemical herbicides in public places such as parks and homeowners lawns, for example, By-laws have recently passed in Calgary, Alberta, and Halifax, Nova Scotia, both in Canada, against their use. Chemical herbicides used in these areas leads to increased chemical exposure to susceptible groups in the population like children, pets, and the elderly.

A number of bacteria and fungi are natural pathogens of weeds and it has been suggested that bioherbicides, or weed killers made from biological agents rather than chemical agents, may provide an alternative to chemical pesticides. For example, U.S. Pat. No. 6,008,159 discloses controlling annual weeds using the fungus *Pyrenophora*. U.S. Pat. Nos. 5,993,802 and 5,472,690 teach suppressing the growth of *Calmagrostis canadensis* using an isolate of a low temperature basidiomycete fungus, or a mycoherbicide (including at least one or both of *Fusarium nivalis* and *Colletotrichum calamagrostidis*), respectively. U.S. Pat. Nos. 5,952,264 and 5,635,444 teach controlling crabgrass using the fungus *Cochliobolus intermedius*, or a fungus selected from the genus *Culvularia*, respectively. U.S. Pat. No. 5,747,029 teaches controlling sicklepod weeds with the fungus *Myrothecium verrucaria*. U.S. Pat. No. 5,698,491 and WO 98/08389 discloses controlling nutsedge weeds with the fungus *Dactylaria higginsii* (WO 98/08389 and U.S. Pat. No. 5,698,491). U.S. Pat. No. 4,606,751 teaches controlling Johnson grass and similar weeds with *Bipolaris sorghicola* spores. The spores are suspended in a solution of water and surfactant and sprayed onto a field onto which the weed is growing. U.S. Pat. No. 5,795,845 discloses a bioherbicidal composition comprising an invert emulsion carrier and a microorganism which is a weakly or non-pathogenic bacterium or fungus. The composition may be used to control pigweed, plumeless thistle, velvet leaf and ground cherry. U.S. Pat. No. 4,636,386 discloses an isolate of *Alternaria* for the control of Italian thistle. U.S. Pat. No. 5,994,27 discloses a composition comprising a bioherbicide which is an isolate of *Sclerotinia minor* which produces foliar wilt and rot in broadleaf weed species so as to inhibit their growth. The bioherbicide may be used to control the growth of broadleaf weeds such as dandelion, broadleaf plantain, ragweed, ivy, knotweed sow thistle and white clover.

Brebaum and Boland (1999, Plant Disease 83:2000) disclose *Phoma exigua* and *Phoma herbarum* as pathogens of dandelion (*Taraxacum officinale*), however, no weed controlling activity was reported using these species.

None of the identified references disclose fungal isolates derived from *Phoma macrostoma* as biocontrol compositions suitable for use to control Canada thistle, dandelion, or other weed species.

There is a need in the art for novel bioherbicides and biocontrol compositions for controlling weeds. Further there is a need in the art for novel bioherbicides and biocontrol compositions for controlling weed plants for example Canada thistle, perennial sowthistle, dandelion, prairie sunflower, field bindweed, wild buckwheat, and scentless chamomile, cleavers, and chickweed. Further, there is a need in the art for biocontrol compositions comprising a biological control agent and a growth medium for supporting the viability of the biological control agent when the biocontrol composition is employed to control weeds.

It is an object of the present invention to overcome disadvantages of the prior art.

The above object is met by a combination of the features of the main claims. The sub claims disclose further advantageous embodiments of the invention.

SUMMARY OF THE INVENTION

The present invention relates to bioherbicides. More specifically, the present invention relates to fungal bioherbicides and compositions comprising fungal bioherbicides.

According to the present invention there is provided a method of controlling one or more broad leaf weeds comprising administering an isolate of *Phoma* cf. *macrostoma*, an extract therefrom, an inoculated broth therefrom, or a combination thereof, to the one or more broad leaf weeds, or to soil where said weeds grow.

The present invention is also directed to the method defined above wherein the one or more broad leaf weeds is a species of a family selected from the group consisting of Compositae, Caryophyllaceae, Convolvulaceae, Plantaginaceae and Rubiaceae. Preferably, the one or more broad leaf weeds is selected from the group consisting of Canada thistle, perennial sowthistle, dandelion, scentless chamomile, false cleavers, chickweed, wild buckwheat, plantain, prairie sunflower and field bindweed.

The present invention also provides a biocontrol agent comprising one or more than one *Phoma* isolate, an extract therefrom, an inoculated broth therefrom, or a combination thereof, wherein the one or more than one *Phoma* isolate, or an extract therefrom, or an inoculated broth therefrom, exhibit weed control activity, growth enhancement activity, or both. The present invention also embraces a biocontrol composition, comprising the biocontrol agent just defined, and a medium for supporting viability of said one or more than one *Phoma* isolate. Preferably, the one or more than one Phoma isolate, is an isolate of *Phoma* cf. *macrostoma*. More preferably, the one or more than one *Phoma* isolate is selected from the group consisting of a) 85-24B (IDAC 230201-1, deposited Feb. 23, 2001),
b) 89-25A (IDAC 110401-1, deposited Apr. 11, 2001),
c) 94-26(IDAC 230201-2, deposited Feb. 23, 2001),
d) 94-44B (IDAC 230201-3, deposited Feb. 23, 2001)
e) 94-134(IDAC 230201-4, deposited Feb. 23, 2001),
f) 94-359A (IDAC 110401-2, deposited Apr. 11, 2001),
g) 95-54A1(IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2(IDAC 110401-4, deposited Apr. 11, 2001), and a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

The present invention also provides a biocontrol agent comprising an extract, or an inoculated broth, from one or more than one *Phoma* cf. *macrostoma* isolate. Preferably, the extract or inoculated broth is obtained from the *Phoma* isolate selected from the group consisting of a) 85-24B (IDAC 230201-1, deposited Feb. 23, 2001),
b) 89-25A (IDAC 110401-1, deposited Apr. 11, 2001),
c) 94-26(IDAC 230201-2, deposited Feb. 23, 2001),
d) 94-44B (IDAC 230201-3, deposited Feb. 23, 2001)
e) 94-134(IDAC 230201-4, deposited Feb. 23, 2001),
f) 94-359A (IDAC 110401-2, deposited Apr. 11, 2001),
g) 95-54A1(IDAC 230201-5, deposited Feb. 23, 2001),
h) 95-268B (IDAC 110401-3, deposited Apr. 11, 2001),
i) 97-12B (IDAC 230201-6, deposited Feb. 23, 2001),
j) 97-15B2(IDAC 110401-4, deposited Apr. 11, 2001), and a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

This invention pertains to the above method wherein the extract is selected from the group consisting of heat killed barley inoculum, a chloroform extract of the *Phoma* isolate, a methanol extract of the *Phoma* isolate, and a ethyl-acetate extract of the *Phoma* isolate, and the inoculated broth is selected from the group consisting of a crude inoculated broth, a filtered inoculated broth, or a centrifuged inoculated broth.

The present invention also pertains to a method of controlling weed development during crop growth comprising:

a) adding an effective amount of a biocontrol agent comprising one or more than one *Phoma* cf *macrostoma* isolate, an extract therefrom, an inoculated broth therefrom, or combination thereof to soil to produce treated soil, the one or more than one *Phoma* cf *macrostoma* isolate, an extract therefrom, or an inoculated broth therefrom, exhibiting weed control activity;
b) planting the crops in the treated soil; and
c) growing the crop.

According to the present invention there is also provided a method of controlling weed development during crop growth comprising:

a) planting the crop,
b) adding an effective amount of said biocontrol agent comprising one or more than one *Phoma* cf *macrostoma* isolate, an extract therefrom, an inoculated broth therefrom, or a combination therefrom, to soil where the crop is planted, the one or more than one *Phoma* cf *macrostoma* isolate, extract therefrom, or inoculated broth therefrom, exhibiting weed control activity;
c) growing the crop.

The present invention is also directed to a method of controlling weed development during crop growth comprising:

a) adding an effective amount of a biocontrol agent comprising one or more than one *Phoma* cf *macrostoma* isolate, an extract therefrom, an inoculated broth therefrom, or a combination thereof, to a crop seed to produce treated crop seed, the one or more than one *Phoma* cf

*macrostoma* isolate, extract therefrom, or inoculated broth therefrom, exhibiting weed control activity;
b) planting the treated crop seed; and
c) growing the crop.

Also included in this invention is the method as just defined wherein the treated crop seed is grass seed, including domestic and specialty turf grass seed, animal pasture or hay seed mixes comprising one or more of timothy, fescue, blue grass, perennial rye grass, bromegrass, canary grass, red top and orchard grass seed.

The methods of the present invention are preferably used to control weed development during growth of a perennial crop. Preferably, the perennial crop is selected from the group consisting of a turf, a perennial grass, and a winter cereal.

The present invention also provides a method of controlling weed development during established crop growth comprising:
a) adding an effective amount of a biocontrol agent comprising one or more than one *Phoma* cf *macrostma* isolate, an extract therefrom, an inoculated broth therefrom, or a combination thereof, to the established crop, the one or more than one *Phoma* cf *macrostoma* isolate, an extract therefrom, or an inoculated broth therefrom, exhibiting weed control activity, and
b) growing the crop.

Also included in this invention is the method as just defined wherein the established crop is grass, including domestic and specialty turf grasses, animal pasture or hay mixes comprising one or more of timothy, fescue, blue grass, perennial rye grass, bromegrass, canarygrass, red top and orchard grass.

The present invention also provides a method of enhancing the growth of a crop, the method comprising:
a) adding an effective amount of a biocontrol agent comprising one or more than one *Phoma* cf *macrostma* isolate, an extract therefrom, an inoculated broth therefrom, or a combination thereof to soil to produce a treated soil;
b) planting the crop in said treated soil, and
c) growing said crop.

The present invention also provides a method of enhancing the growth of a crop, the method comprising:
a) planting said crop in soil;
b) adding an effective amount of a biocontrol agent comprising one or more than one *Phoma* cf *macrostma* isolate, an extract therefrom, an inoculated broth therefrom, or a combination thereof to the soil where said crop is planted; and
c) growing said crop.

The present invention further provides a method of enhancing the growth of an established crop, the method comprising:
a) adding an effective amount of a biocontrol agent comprising one or more than one *Phoma* cf *macrostma* isolate, an extract therefrom, an inoculated broth therefrom, or a combination thereof to the established crop; and
b) growing the crop.

Also included in this invention is the methods as just defined wherein the crop is grass, including domestic and specialty turf grasses, animal pasture or hay mixes comprising one or more of timothy, fescue, blue grass, perennial rye grass, bromegrass, canarygrass, red top and orchard grass.

The present invention is also directed to a method of enhancing the growth of a crop, the method comprising:
a) adding an effective amount of a biocontrol agent comprising one or more than one *Phoma* cf *macrostoma* isolate, an extract therefrom, an inoculated broth therefrom, or a combination thereof, to a crop seed to produce treated crop seed;
b) planting the treated crop seed; and
c) growing the crop.

Also included in this invention is the method as just defined wherein the treated crop seed is grass seed, including domestic and specialty turf grass seed, animal pasture or hay seed mixes comprising one or more of timothy, fescue, blue grass, perennial rye grass, bromegrass, canary grass, red top and orchard grass seed.

The methods of the present invention also relate to the use of a biocontrol composition comprising one or more than one *Phoma* cf *macrostma* isolate, an extract therefrom, an inoculated broth therefrom, or a combination thereof; and a medium for supporting viability of the one or more than one *Phoma* cf *macrostma* isolate.

The present invention also provides for any of the above methods wherein the biocontrol agent or composition is applied to the soil before or after emergence of the weed, preferably before emergence.

The present invention also provides for any of the above methods wherein the biocontrol agent or composition is applied by dusting, rubbing, spreading, drilling, banding, broadcasting, spraying, liquid injection, pouring or soil drenching.

The present invention embraces a coated crop seed comprising one or more Phoma isolates and a binder. The invention also includes a coated crop seed comprising an extract obtained from one or more *Phoma* isolates and a binder. The crop seed that is coated is preferably grass seed, including domestic and specialty turf grass seed, animal pasture or hay seed mixes comprising one or more of timothy, fescue, blue grass, perennial rye grass, bromegrass, canary grass, red top and orchard grass seed.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
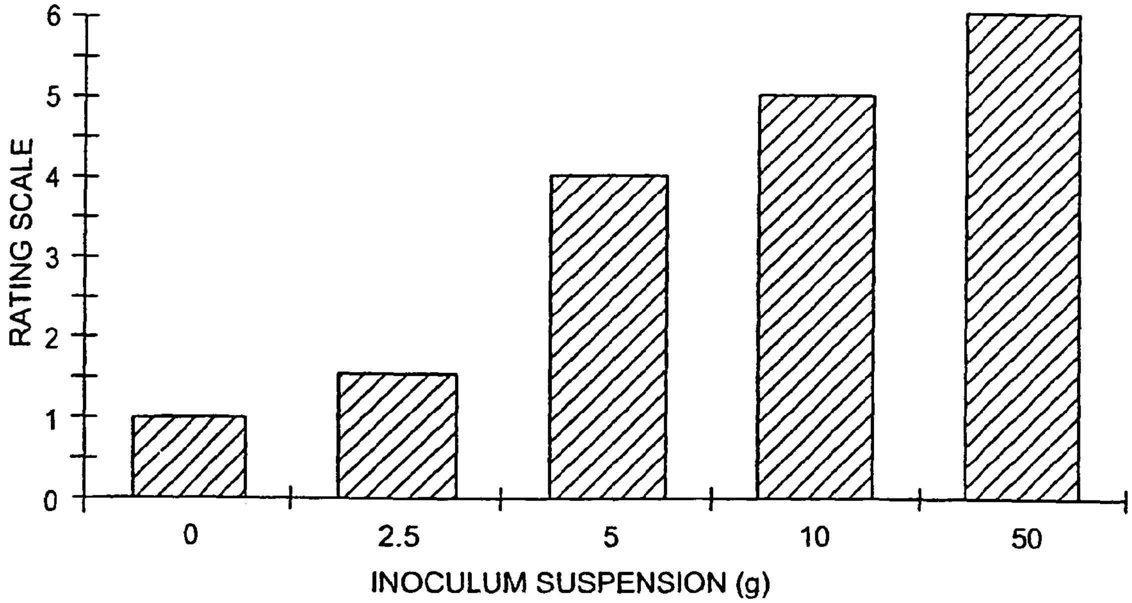
FIG. 1 shows the effect of different amounts of inoculum suspension 85-24B on Canada thistle plants. The Rating scale is: 1=healthy, dark green foliage; 2=slightly yellow-green foliage; 3=leaves primarily yellow, some yellow-green; 4=leaves primarily white, a few yellow-green; 5=slants completely white; and 6=plants dead.

The present invention relates to bioherbicides. More specifically, the present invention relates to fungal bioherbicides and compositions comprising fungal bioherbicides.

The following description is of a preferred embodiment by way of example only and without limitation to the combination of features necessary for carrying the invention into effect.

By the term “controlling weed growth”, or “weed control activity” it is meant that one or more fungal isolates, an extract therefrom, an inoculated broth therefrom, or a combination thereof, when applied on or near a weed interferes with the normal growth and development of a weed. Examples of weed growth control activity include, but are not limited to, inhibition of root growth, inhibition of shoot growth, inhibition of shoot emergence, reduction of weed biomass inhibition of seed production, or the ability to induce chlorosis, or reduce competitiveness of a weed for water, nutrients, or a combination thereof, that would otherwise be utilized by a crop plant. Alternatively, the fungal isolate may be capable of controlling weeds by killing them. It is preferred that a fungal isolate selectively controls weed growth, and does not have any substantial effect on a plant for which growth is desired, for example a non-target plant such as an agriculturally important plant, or a residential or commercial grass.

Fungal isolates that control weed growth or the exhibit weed control activity may be characterized as having a Weed Control Index (WCI) of between about 20% to 100% (the higher the WCI, the more efficacious the fungal isolate). The WCI includes either an annual WCI (WCIA) or a perennial WCI (WCIP) as defined below. Preferably, fungal isolates are characterized as having a WCI of between about 50% to 100%. More preferably, the fungal isolates have a WCI of between about 70% to 100%. However, it is to be understood that a fungal isolate with a low WCI may still prove effective to help control weed growth and provide a non-target plant a competitive advantage over one or more weeds. Furthermore it may be desirable to use one or more fungal isolates that exhibit a low WCI in order to ensure that a non-target plant is not affected by the bioherbicide.

The weed control Index is determined using either WCIA for evaluation of annual weeds, or WCIP, for evaluation of perennial weeds, as follows:

$$WCIA=\{[(100-FFW)+(\%\,M)+(\%\,IOC)]/300\}\times 100\%$$

$$WCIP=\{[(100-RW)+(100-FFW)+(\%\,M)+(\%\,IOC)]/400\}\times 100\%$$

where

RW—is root weight

FFW—is foliar fresh weight;

M—is mortality; and

IOC—is incidence of chlorosis, as determined by number of plants with a rating of 3-6, where, 1=healthy, dark green foliage; 2=slightly yellow-green foliage; 3=leaves primarily yellow, some yellow-green; 4=leaves primarily white, a few yellow-green; 5=plants completely white; and 6=plants dead.

By "fungal isolate" it is meant a biologically active *Phoma* species, or a biologically active fragment, component, obtained or isolated from a *Phoma* spp. By fragment or component of a fungal isolate, it is meant a fragment of the mycelium, or one or more spores, pycnidia, conidia, chlamydospores or a combination thereof, obtained from the fungi. Fungal isolates may be obtained from small chlorotic and necrotic lesions on leaf and stem tissues of a desired weed, for example but not limited to Canada thistle and assayed for weed growth control activity, as described herein or using standard methods as would be known to one of skill in the art. Preferably, the fungal isolates are strains of *Phoma* cf. *macrostoma*. Examples of *Phoma* cf. *macrostoma* isolates, which may be used according to the present invention, and which are not to be considered as limiting in any manner, include:

85-24B (IDAC 230201-1, deposited Feb. 23, 2001),
89-25A (IDAC 110401-1, deposited Apr. 11, 2001),
94-26(IDAC 230201-2, deposited Feb. 23, 2001),
94-44B (IDAC 230201-3, deposited Feb. 23, 2001)
94-134(IDAC 230201-4, deposited Feb. 23, 2001),
94-359A (IDAC 110401-2, deposited Apr. 11, 2001),
95-54A1(IDAC 230201-5, deposited Feb. 23, 2001),
95-268B (IDAC 110401-3, deposited Apr. 11, 2001),
97-12B (IDAC 230201-6, deposited Feb. 23, 2001),
97-15B2(IDAC 110401-4, deposited Apr. 11, 2001), or a combination thereof. The *Phoma* cf. *macrostoma* isolates are deposited at the International Depositary Authority of Canada (IDAC), Bureau of Microbiology, Health Canada, 1015 Arlington Street, Winnipeg, Manitoba, R3E 3R2 Canada.

By "extract", it is meant an aqueous or solvent extract, crude or in a more purified state, comprising one or more active compounds obtained from a fungal isolate, that in the proximity of, or when applied onto, a weed is capable of controlling weed growth.

By an "inoculated broth", it is meant the broth obtained from a culture of one or more than one *Phoma* isolates (see Example 5) as defined herein, that comprise one or more active compounds capable of controlling weed growth. An inoculated broth may be concentrated using methods known in the art, for example, but not limited to evaporation, roto-evaporation or freeze drying.

By "saturation" it is meant the maximum retention capacity of a soil, and is defined as occuring when the soil pores in the upper part of the soil are filled with water. By "field capacity" or "field moisture capacity", it is meant the percentage of water remaining in a soil two or three days after having been saturated and after free drainage has essentially ceased.

By "permanent wilting point" it is meant the critical moisture of soil as which plants wilt and fail to recover turgidity when placed in a dark and humid atmosphere.

In a preferred embodiment, the fungal isolate is formulated in a biocontrol composition comprising one or more fungal isolates, one or more extracts obtained from a fungal isolate, an inoculated broth, or a combination thereof, and the biocontrol composition is added to soil, added to compost, added to peat-type pellets, added to or used to coat a planting medium, for example but not limited to wood chips, used to coat or treat plant seed in the presence of a binder, for example but not limited to methylcellulose, starch, clay, sugar or a combination thereof, or applied to a plant, for example but not limited to, spraying or rubbing on a plant, to control weeds. Furthermore, liquid injection may be used to apply one or more isolates, for example, spores or mycelia, extracts obtained from fungal isolates, inoculated broth, or a combination thereof, to soil. Liquid injection may used for perennial applications, for example but not limited to turf grass management.

By the term "biocontrol composition", it is meant a composition comprising one or more than one biocontrol agent of the present invention within a suitable medium. A biocontrol agent consists of one or more fungal isolates as defined above, an inoculated broth therefrom, an extract therefrom, or a combination thereof. For example, if the biocontrol composition comprises a fungal isolate, then the suitable medium may comprise a growth medium to maintain the viability of the fungal isolate before, and after application of the biocontrol composition to the soil. If an extract of a fungal isolate, one or more fungal isolates, or a combination thereof, is used for administration to a weed or soil, then the suitable medium may comprise stabilizing agents, surfactants and the like as would be known to one of skill in the art. For example, which is not to be considered limiting in any manner, media may include supplemented Agar, pesta, peat prills, vermiculite, clay, starches, potato dextrose broth (PDB), V8® juice broth, whole grain or grain fragments of, for example but not limited to, legume grains including lentil or chickpea, or cereal grain for example, wheat or barley, or corn, or any combination or variant thereof, provided that the medium allows the fungal isolate to remain viable.

Pesta is a term for a granular product made from a cereal grain flour and a biocontrol agent. The process encapsulates biocontrol agents in pasta-like products called pesta (Connick et al., 1991, which is incorporated herein by reference). Bacteria formulated in such media may exhibit extended shelf and field-life (e.g. Connick et al., 1996; Connick et al., 1998). These characteristics are desired in a product which may be stored prior to use or shipped over long-distances prior to being used for weed control in a field. Therefore, the biocontrol compositions comprising fungal isolates of the present invention may be formulated in a suitable medium for example, but not limited to, pesta.

If the suitable medium is a growth medium, then the growth medium may comprise any liquid, semi-liquid or solid medium which allows the fungal isolates of the present invention to grow or remain viable. Any growth medium known in the art to which is capable of supporting the fungal isolate may be employed. Examples of suitable growth media, which are not to be considered limiting in any manner include potato dextrose agar, potato dextrose broth, V8® juice broth and the like. Preferably, the growth medium is a solid medium, for example but not limited to grain, for example whole grain or fragments thereof, for example but not limited to, legume grains including lentil or chickpea, or cereal grain for example, wheat or barley, or corn (see Example 3). The growth medium should also permit an effective amount of the fungal isolate to remain viable after being applied to the soil of a crop for a suitable period of time, for example but not limited to, up to about 7 days to about 18 months after application. Preferably, the isolate remains viable from about 14 days to about 12 months, and more preferred, from about 14 days to about 90 days. For soil application, spores, mycelia (growing on grain), or spores and mycelia growing on grain may be mixed together and either applied onto, or mixed with, soil. Furthermore, liquid injection may be used to apply one or more isolates, for example, spores or mycelia, extracts obtained from fungal isolates, or a combination thereof to soil. Typical application rates for a fungal isolate that was grown on the preferred growth medium include, but are not limited to, 0.001 $kg/m^2$ to 5 $kg/m^2$ using a particle size between 49-840 microns and particle viability of 60-100%. The preferred rate of application is 0.1 $kg/m^2$ to 1.0 $kg/m^2$. However, any application rate that results in weed control activity may be employed.

When one or more fungal isolates are applied using a solid medium, for example hulless barley, the infested barley grain prepared as described in Example 3 may be ground prior to application to soil. Any suitable granule size may be used, for example, from about 50µ to about 1 mm. The preferred viability of the particles used for application is about 60-100%. As shown in Table 20 (Example 3), with smaller granule size, a lower application dose rate ($g/m^2$)will achieve a similar, or better, weed control activity.

It is also contemplated by the present invention that more than one fungal isolate may be used to control weeds. Similarly, a biocontrol composition may comprise more than one fungal isolate. Multiple fungal isolates capable of controlling a specific weed may be used or multiple fungal isolates, each of which is capable of controlling a distinct type of weed may be mixed and used as described herein. It is also preferred that the fungal isolate or biocontrol composition exhibit host selectivity, in that weed control activity is observed in one or more target weeds, while no weed control activity is observed on non-target plants. Examples of non-target plants include agriculturally important plants, and domestic or commercial grasses (Gramineae).

By weed, it is meant any undesired plant. Preferably, a weed is a broad-leaf (dicot) weed, for example but not limited to members of the Compositae, Caryophyllaceae, Polygonaceae, Convolvulaceae, Plantaginaceae and Rubiaceae. More preferably, a weed is selected from the group consisting of:

Compositae (Composite family): including dandelion [*Taraxacum officinale* L.], ox-eye daisy [*Chrysanthemum leucanthemum*], burdocks for example common burdock [*Arctium minus*], goat's beards [e.g. *Tragopogon dubius*], cockleburs [e.g. *Xanthium strumarium*], ragweeds for example common ragweed [*Ambrosia artemisiifolia*] or giant ragweed [*Ambrosia trifolia*], scentless chamomile [*Matricaria perforata* Mérat.], sow-thistles, for example perennial sowthistle [*Sonchus arvensis* L.], and thistles, for example Canada thistle [*Cirsium arvense* L.(Scop.)];

Caryophyllaceae (Pink Family): including chickweed [*Stellaria media* (L.)Vill.];

Polygonaceae (Buckwheat Family): including wild buckwheat [*Polygonum convolvulus* L.];

Convolvulaceae (Morning Glory Family): including field bindweed [*Convolvulus arvensis* L.];

Plantaginaceae (Plantain Family): including plantain [*Plantago lanceolata*]; or Rubiaceae (Rubus family): including false cleavers (*Gallium spurium*)

Preferably, the fungal isolates, biocontrol compositions, or both, of the present invention are added to the soil where the seed either grows or may grow. The soil may be mixed so that one or more fungal isolates are in close proximity to the root system or root fragments of the weeds. It is also preferable that the fungal isolates be in close proximity to weed seeds when such seeds are present. The fungal isolates and biocontrol compositions of the present invention may be applied to soil or weed by any method known in the art such as, but not limited to dusting, rubbing, spreading, drilling, banding, broadcasting (with or without incorporation), spraying, liquid injection, pouring or soil drenching. The fungal isolates and biocontrol compositions may also be applied at any suitable time, for example but not limited to, during or after soil tillage. Preferably, the biocontrol composition is applied during the spring, or early summer. Solid preparation of the fungal isolate alone, or biocontrol composition for example but not limited to infested barley grain, is added to soil in the amount of about 0.1 $kg/m^2$ to about 5 $kg/m^2$. Liquid suspensions of about $10^3$ to about $10^9$ cfu/mL, may be applied at a rate of about 1 $L/m^2$ to about 5 $L/m^2$. However, any amount that results in weed controlling activity may be applied.

It is also within the scope of the present invention, that extracts obtained from one or more fungal isolates may be formulated and applied to the soil or weed as a liquid, for example as a spray, injection, drench, rubbing, dusting, or as a solid, including autoclaved infested barley granules dusting or rubbing of suitably formulated extracts. As one of skill will be able to determine, appropriate dosages will depend upon the concentration of active components within the extract or solid. Preferably, the extract is derived from either a 4 week old crude broth concentrated about 100× the original volume, or from an extract obtained from a 3:1 ratio of extracted mycelium to methanol. An example, which is not to be considered limiting, of an application rate of such extracts is from about 0.1 to about 2.5 $L/m^2$, depending upon the concentration of active ingredients. However, any amount that results in weed controlling activity may be applied.

A biocontrol agent, or a biocontrol composition, of the present invention comprising one or more fungal isolates, one or more extracts obtained from a fungal isolate, an inoculated broth, or a combination thereof may be added to a planting medium, for example compost, or it may be added to or used to coat alternate planting media, for example but not limited to wood chips, landscaping cloth, vermiculite and the like, as would be evident to one of skill in the art. Furthermore, the biocontrol agent or biocontrol composition as described herein may be used to coat or treat plant seed. Coated seed may involve the use of a binder, for example but not limited to methylcellulose, starch, clay, sugar or a combination thereof.

Therefore, according to the present invention, there is provided a method of controlling a range of weeds with a bioherbicide comprising one or more fungal isolates, a biocontrol agent, or a biocontrol composition comprising one or more fungal isolates, an extract obtained from one or more fungal isolates, an inoculated broth, or a combination thereof. Fungal isolates, or a combination thereof, which may be employed to control weed growth include, but are not limited to those listed in Table 1 below.

TABLE 1

| Fungal isolate | Target Weed | Deposit information |
|---|---|---|
| *Fungal Isolates Information and Target Weeds Affected* | | |
| 95-54A1 | Canada thistle, Scentless chamomile, False cleavers, Chickweed, Field bindweed, Dandelion, Plantain, Prairie sunflower, | IDAC 230201-5* |
| 97-12B | Canada thistle, Dandelion, Scentless Chamomile, False cleavers, Perennial sowthistle, Chickweed | IDAC 230201-6* |
| 97-15B2 | Canada thistle, Scentless chamomile, False cleavers, Chickweed, Wild buckwheat, Prairie sunflower | IDAC 110401-4** |
| 94-359A | Scentless chamomile, Canada thistle, Dandelion | IDAC 110401-2** |
| 89-25A | Canada thistle, scentless chamomile, dandelion, Prairie sunflower | IDAC 110401-1** |
| 85-24B | Canada thistle, Dandelion, Scentless chamomile, False cleavers, Prairie Sunflower, chickweed, Plantain, wild buckwheat | IDAC 230201-1* |
| 94-26 | Canada thistle, Dandelion, Scentless chamomile, False cleavers, Perennial sowthistle, Chickweed, Plantain, wild buckwheat | IDAC 230201-2* |
| 94-44B | Canada thistle, Dandelion, Scentless chamomile, False cleavers, Perennial sowthistle, Chickweed, Wild buckwheat, Plantain, Prairie sunflower | IDAC 230201-3* |
| 94-134 | Canada thistle, Chickweed, Wild buckwheat, Scentless chamomile, Plantain, False cleavers, | IDAC 230201-4* |
| 95-268B | False cleavers, Chickweed, Wild buckwheat, Scentless chamomile, Canada thistle, dandelion | IDAC 110401-3** |

*deposited Feb. 23, 2001 at the International Deposit Authority of Canada (IDAC), Bureau of Microbiology, Health Canada, 1015 Arlington Street, Winnipeg, Manitoba, R3E 3R2 Canada.
**deposited Apr. 11, 2001 at the International Deposit Authority of Canada (IDAC), Bureau of Microbiology, Health Canada, 1015 Arlington Street, Winnipeg, Manitoba, R3E 3R2 Canada.

Referring now to Table 2 (and see Example 2 for associated protocols) there is shown, as an example, weed control activity, as indicated by a reduction of foliar fresh weight, reduction in root weight, chlorosis, or mortality, in Canada thistle by a range of fungal isolates.

TABLE 2

Effect of fungal isolates on foliar fresh weight (FFW), root weight (RW), mortality (M) and incidence of Chlorosis (IOC) on Canada Thistle plants, and associated Weed Control Index (WCIP)

| Isolates | % FFW* | % RW* | % M | % IOC | WCIP** |
|---|---|---|---|---|---|
| Control | 100 ± 4 | 100 ± 5 | 1 ± 1 | 0 | 0 |
| 85-24B | 22 ± 6 | 25 ± 4 | 57 ± 7 | 86 ± 6 | 74 |
| 94-26 | 23 ± 7 | 26 ± 6 | 72 ± 7 | 83 ± 6 | 76 |
| 94-44B | 8 ± 3 | 15 ± 2 | 80 ± 5 | 96 ± 2 | 88 |
| 94-134 | 20 ± 8 | 26 ± 5 | 59 ± 11 | 74 ± 9 | 72 |
| 95-54A1 | 20 ± 10 | 23 ± 8 | 79 ± 8 | 82 ± 8 | 79 |
| 97-12B | 59 ± 13 | 53 ± 11 | 39 ± 11 | 61 ± 11 | 47 |
| 89-25A | 76 ± 13 | 63 ± 11 | 23 ± 8 | 36 ± 10 | 30 |
| 94-359A | 69 ± 13 | 63 ± 10 | 18 ± 9 | 43 ± 13 | 32 |
| 95-268B | 31 ± 7 | 32 ± 6 | 58 ± 8 | 75 ± 7 | 68 |
| 97-15B2 | 17 ± 4 | 17 ± 4 | 81 ± 8 | 89 ± 6 | 85 |

*% of control
**WCIP = {[(100 − RW) + (100 − FFW) + (% M) + (% IOC]/400} × 100%.

From Table 2, it can be noted that several fungal strains, for example but not limited to, 85-24B, 94-26, 94-44B, 94-134, 95-54A1, 97-12B, 95-268B and 97-15B2 are capable reducing foliar fresh weight in Canada thistle from about 40% to about 92%, and of suppressing root weight by about 47% to about 85% compared to the uninoculated control. These fungal isolates are characterized as having a WCIP from about 47 to 88% and they are effective in controlling weed growth which is supported by the observation that up to about 80% of the plants are killed by the treatment. Fungal isolates 89-25A and 94-359A are also effective at suppressing foliar fresh weight, root weight, and exhibit a WCIP of about 30-32%.

Therefore, the present invention is directed to a bioherbicide comprising fungal isolates 85-24B, 94-26, 94-44B, 94-134, 95-54A1, 97-12B, 89-25A, 94-359A, 95-268B, 97-15B2, or a combination thereof for the control of Canada thistle.

Referring now to FIG. 1, there is shown the effect of an inoculum suspension comprising fungal isolate 85-24B on Canada thistle. FIG. 1 demonstrates that damage to Canada thistle was greater at higher inoculum levels. A dose in the range of about 5 g/0.01 $m^2$ to about 50 g/0.01 $m^2$ or higher is capable of controlling Canada thistle. Similar result were also observed by applying granules of infested barley grain to the soil.

Without wishing to be bound by theory, the fungal isolates as described herein may have the ability to weaken Canada thistle, or a range of other perennial or annual weeds, as described below, by affecting processes involved in plant growth and development, for example photosynthesis, the accumulation of storage products in the roots, reducing shoot emergence, reducing root growth, inducing symptoms of chlorosis (yellowing of plant leaves).

Characterization of the weed control activity of several fungal isolates of the present invention indicates that weed control activity of a fungal isolate may last about one growing season, depending upon the time of application of the fungal isolate to the soil or plant. With reference to Table 18 (Example 3), it is shown that spring or summer application of a fungal isolate exhibits weed control activity over one or more growth seasons. Fall application results in no observed weed control activity. Furthermore, as shown in Table 19 (Example 3), weed control activity increases with higher soil moisture content.

A number of fungal isolates were also tested to determine their efficacy at controlling weeds other than Canada thistle, for example, members of the Aster family including *Sonchus arvense* (perennial sowthistle), *Helianthus* (prairie sunflower), *Taraxacum officinale* (dandelion), *Matricaria perforata* (scentless chamomile), and other plants, including chickweed (*Stellaria media*), wild oats, green foxtail, and false cleavers (*Gallium spurium*).

Figure 2:
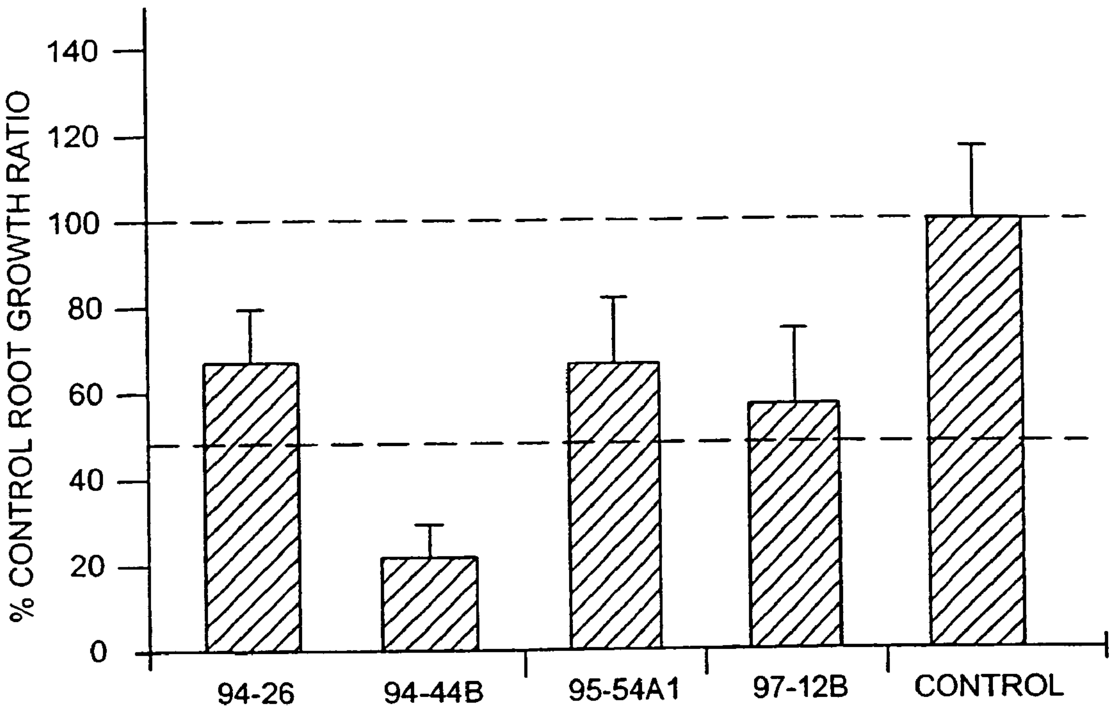
FIG. 2 shows the effect of fungal isolates 94-44B, 94-26, 95-54A1 and 97-12B on the root growth ratio of perennial sowthistle.
Figure 3:
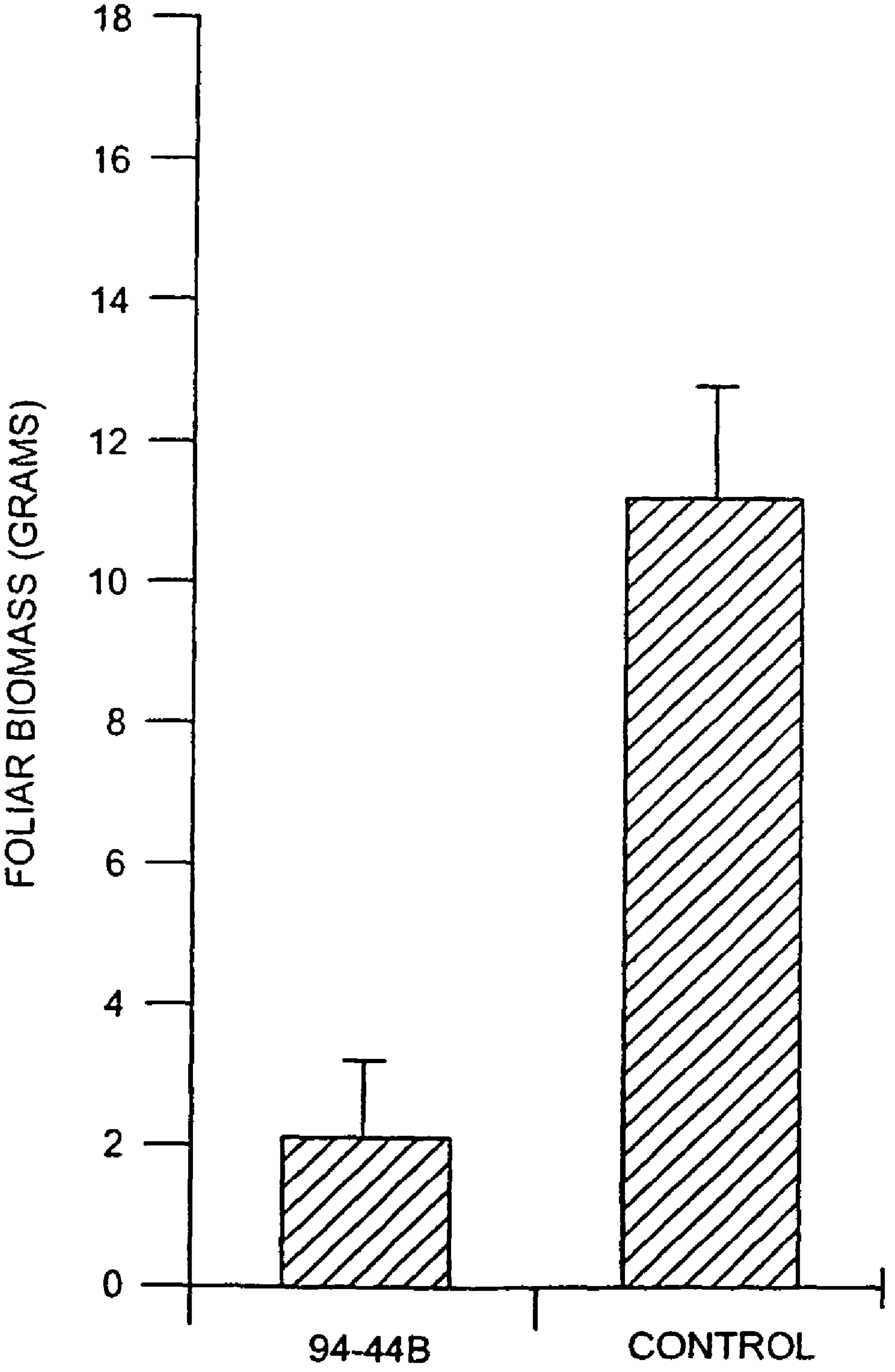
FIG. 3 shows the effect of fungal isolate 94-44B on foliar biomass of perennial sowthistle.
Figure 4:
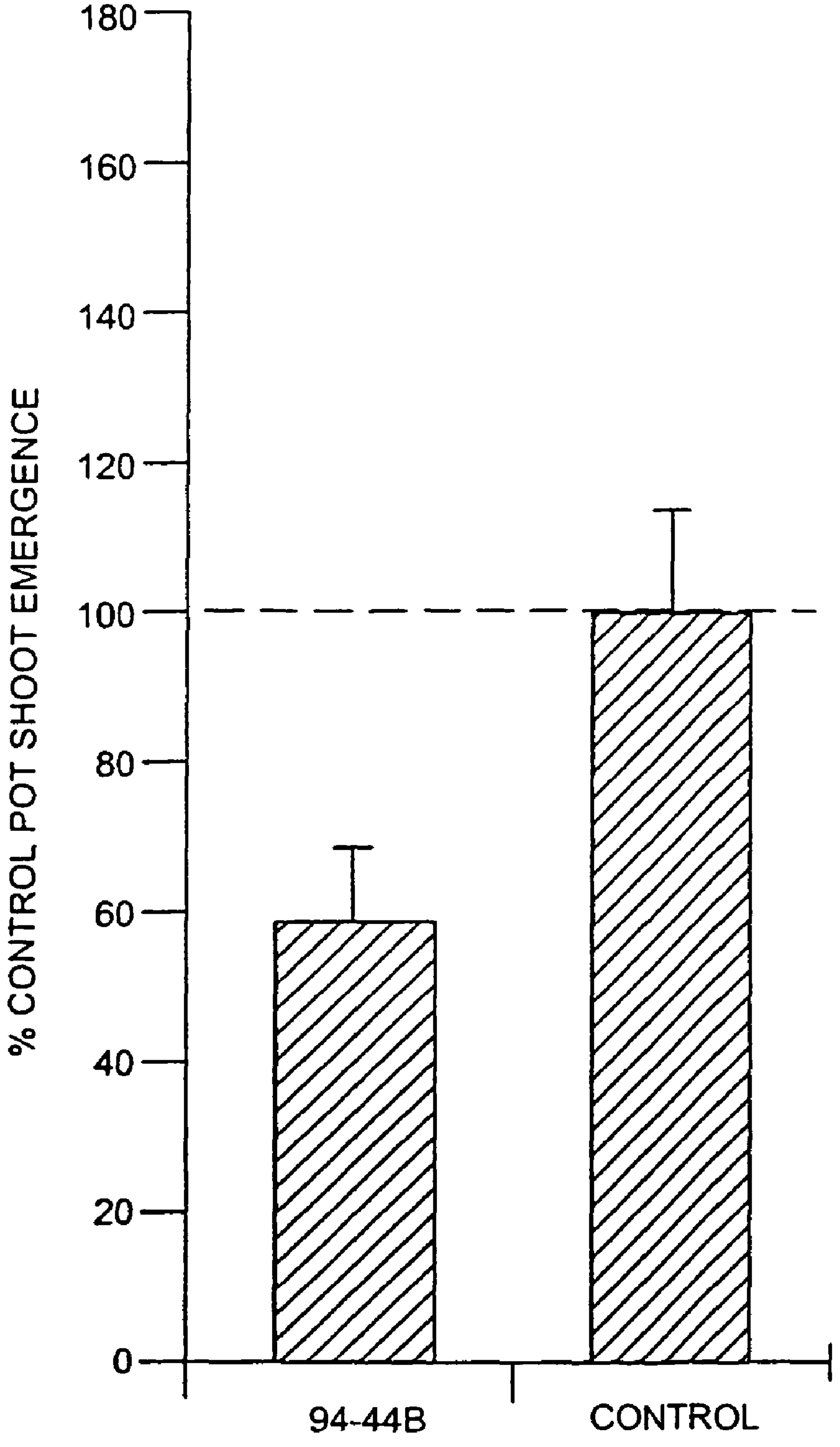
FIG. 4 shows the effect of fungal isolate 94-44B on shoot emergence of perennial sowthistle.
Figure 5:
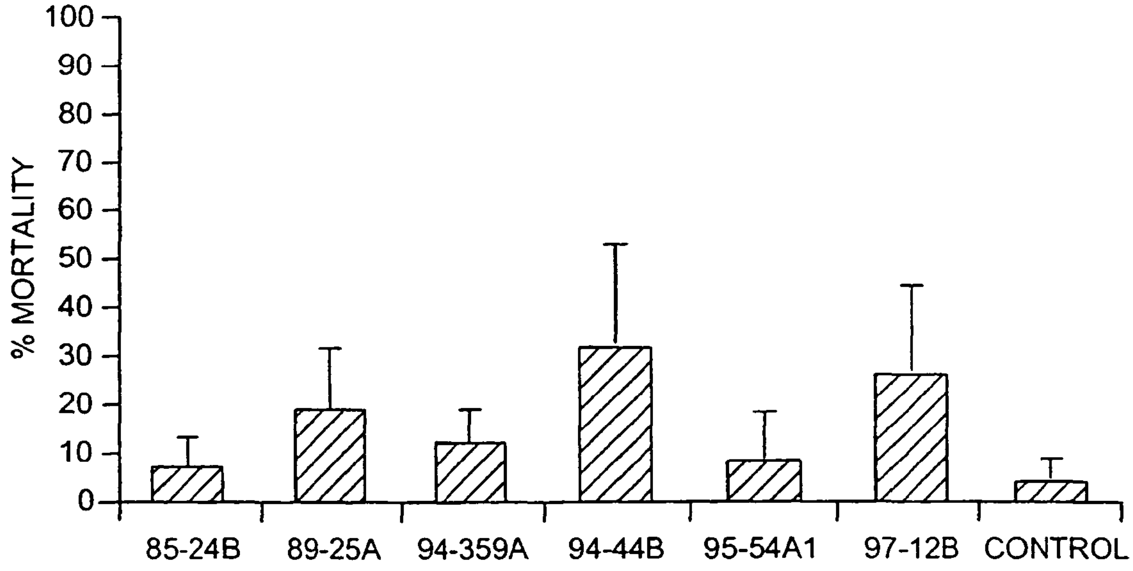
FIG. 5 shows a graphical representation of weed mortality following application of fungal isolate 94-44B, 89-25A and 97-12B to perennial sowthistle.

Fungal isolates 85-24B, 89-25A, 94-26, 94-359A, 94-44B, 94-134, 95-54A1, 95-268B, 97-15B2 and 97-12B were applied to perennial sowthistle using the inoculum mat bioassay described in Example 2. As shown in FIG. 2, fungal isolates 94-44B, 94-26, 95-54A1 and 97-12B reduced the weight of roots compared to the uninoculated control in greenhouse trials. A similar reduction in root weight was also observed with most of the other fungal isolates as indicated in Table 8 of Example 2. Further, fungal isolate 94-44B significantly reduced foliar biomass (FIG. 3) and reduced shoot emergence (FIG. 4) relative to the control. Three isolates (94-44B, 89-25A, and 97-12B) increased the mortality of the weed as shown in FIG. 5 and Table 8.

Therefore, fungal isolates 94-44B, 89-25A, 94-26, 95-54A1 and 97-12B may be used to control perennial sowthistle (*Sonchus arvensis*). In a preferred embodiment, fungal isolate, or a biocontrol composition comprising 94-44B is used to control perennial sowthistle.

Similar results have been observed of the effect of these fungal isolates on other weeds, both perennial and annual weeds, as demonstrated by determining the WCI's for a range of weed species, for example as shown in Table 3 (also see Example 2).

TABLE 3

Weed control index (WCI) of fungal isolates on scentless chamomile (SC), false cleavers (FC), prairie sunflower (SF), chickweed (CH), wild buckwheat (WB), field bindweed (FB), perennial sow thistle (PST), dandelion (DA), and Canada thistle (CT).

| Isolate | SC* | FC* | SF* | CH* | WB* | FB* | PST** | DA** | CT** |
|---|---|---|---|---|---|---|---|---|---|
| No fungus | 7 | 4 | 0 | 0 | 0 | 3 | 0.1 | 0 | 0 |
| 85-24B | 79 | 30 | 84 | 76 | 92 | nd | 7 | 62 | 74 |
| 94-26 | 27 | 48 | nd | 91 | 39 | nd | 24 | 47 | 76 |
| 94-44B | 82 | 64 | 69 | 99 | 96 | nd | 58 | 59 | 88 |
| 94-134 | 82 | 54 | 6 | 59 | 85 | nd | 8 | 15 | 72 |
| 95-54A1 | 98 | 54 | 72 | 59 | 85 | nd | 8 | 15 | 72 |
| 97-12B | 93 | 43 | 9 | 57 | 15 | nd | 34 | 61 | 47 |
| 89-25A | 71 | 13 | 70 | nd | 13 | nd | 15 | 43 | 30 |
| 94-359A | 50 | 18 | 3 | nd | 17 | 13 | 6 | 25 | 32 |
| 95-268B | 72 | 92 | 0 | 97 | 81 | nd | 0 | 45 | 68 |
| 97-15B2 | 91 | 72 | 53 | 65 | 55 | nd | 7 | 9 | 85 |

nd = not determined

*WCIA(%) = {[(100 − FFW) + (% M) + (% IOC)] ÷ 300} × 100%.

**WCIP (%) = {[(100 − RW) + (100 − FFW) + (% M) + (% IOC)] ÷ 400} × 100%.

Therefore, the present invention is also directed to a bioherbicide comprising fungal isolates 85-24B, 94-26, 94-44B, 94-134, 95-54A1, 97-12B, 89-25A, 94-359A, 95-268B, 97-15B2, or a combination thereof, for the control of any susceptible weed, both annual and perennial. Preferably the weed is a broad leaf weed. More preferably, the broad leaf weed is from Compositae, Caryophyllaceae, Polygonaceae, Plantaginaceae, Rubiaceae, or Convolvulaceae, for example but not limited to, scentless chamomile, false cleavers, chickweed, wild buckwheat, field bindweed, perennial sow thistle, dandelion, and Canada thistle.

Using the inoculum mat bioassay (method outlined in Example 2), a number of fungal isolates were tested for their ability to control sunflower (*Helianthus*) weeds. Germination of seed was affected by fungal isolate 85-24B, which reduced sunflower seed germination by about 10%. Five fungal isolates (85-24B, 94-44B, 89-25A, 95-54A1, 97-15B2) reduced foliar biomass in prairie sunflower (also see Table 10(B), Example 2). Thus, fungal isolates 85-24B, 94-44B, 89-25A, 95-54A1, 97-15B2 may be used to control prairie sunflower.

It has also been observed that these fungal isolates and biocontrol compositions comprising the fungal isolates of the present invention are specific for a target group of weed plants, for example, those of the Aster (Compositae) family. Generally, the fungal isolates of the present invention were not effective in controlling growth of grasses, for example, wild oats, and green foxtail (see Table 12 and 13, respectively). However, 94-44B exhibits weed control activity in wild oats, and 85-24B and 95-359A exhibits weed control activity in green foxtail (see Table 17, Example 2 for summary of WCI's).

The fungal isolates of the present invention also exhibit selectivity in that, even under high inoculum loads (significantly higher than that used under field conditions), isolates can be identified that induce negligible, or no, disease symptoms in crop plants (see Tables 22 and 23, Example 4). Example of crop plants tested include:

1) Cereal and other monocots
   - Wheat—cvs. Katepwa, AC Domain, AC Karma, Biggar, Kyle
   - Barley—cvs. Harrington, Silky
   - Oat—cvs. Derby or Walden
   - Millet—cvs. Minco or Prairie Gold
   - Canary seed—cv. Keet
2) Oilseed crops
   - Canola—cvs. AC Excel, AC Parkland
   - Mustard—cvs. Cutlas, Ochre
   - Flax—cv. Vimy
   - Sunflower—cvs. Cargill SF270 or IS7111
   - Safflower—cv. Lethbridge
3) Pulse crops
   - Lentil—cvs. Laird, Eston
   - Field pea—cv. Express
   - Chickpea—cv. Sanford
   - Faba bean—cv. CDC Fatima
4) Forage crops
   - Clovers—yellow clover cv. Norgold, white clover cvs. Polara and Sonja, common clover,
   - red clover cvs. Altaswede or Florex
   - Birdsfoot trefoil—cv. Cree
   - Alfalfa—cv. Beaver For example, which is not to be considered limiting in any manner, 94-44B is suitable for use with cereal crops, as even under high inoculum loads no disease symptoms are observed. However, the use of 94-44B under high inoculum loads may not be desired for use on pulse crops, as pulse crops exhibit some disease symptoms under these conditions. If lower inoculum loads of 94-44B are used, then the disease symptoms in pulse are minimized and this fungal isolate may be used with pulse crops. At reduced inoculum loads, these isolates still exhibit weed control activity. One of skill in the art may manipulate the dosage to optimize the balance between obtaining weed control activity and avoiding disease symptoms in a non-target crop, agriculturally or commercially important plant.

Also contemplated by the present invention is the use of an inoculated broth, or an extract from one or more of the fungal isolates of the present invention as a weed control agent. As described in Example 5, an inoculated broth (including a concentrated inoculated broth), aqueous or solvent extracts, obtained from one or more fungal isolates as described herein, and reconstituted in an appropriate medium, for example, but not limited to water or methanol, may be applied to the soil or leaf of a plant and exhibit weed control activity. It is also contemplated that an inoculated broth, or an extract of the present invention may be combined with a chemical herbicide, or a fungal isolate, including non-Phoma isolates as a weed control agent.

Also contemplated by the present invention is a method using one or more than one *Phoma* cf *macrostma* isolate, an extract therefrom, an inoculated broth therefrom, or a combination thereof for controlling weed development during growth of an establishing or established crop, for example, as listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example, in Table 18A (Example 3).

The present invention further contemplates a method using one or more than one *Phoma* cf *macrostma* isolate, an extract therefrom, an inoculated broth therefrom, or a combination thereof for enhancing the growth (e.g. increasing biomass) of an establishing or established crop, for example, as listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example, in Tables 18A (Example 3), 21(C) and 21(D) (Example 3). Without wishing to be bound by theory, enhancement of growth may be a result of an increase in the rate of germination.

Also contemplated by the present invention is a method using one or more than one *Phoma* cf *macrostma* isolate, an extract therefrom, an inoculated broth therefrom, or a combination thereof for controlling weed development during growth of an establishing or established crop by foliar spray application before or after emergence of the weed. The crop can be, for example, one of the crops listed above, and including, but not limited to a grass, such as, but not limited to domestic and specialty turf grasses, animal pasture or hay mixes comprising one or more of timothy, fescue, blue grass, perennial rye grass, bromegrass, canary grass, red top and orchard grass, as illustrated, for example in Table 21(D) (Example 3).

The application of an inoculated broth, or an extract of the present invention, when combined with an fungal isolate, exerts weed controlling activity in a rapid manner, when compared to applying an isolate on its own. Without wishing to be bound by theory, the inoculated broth, or extract is able to function in a more rapid manner, since there is no requirement for growth of the fungal isolate, and associated production of the one or more compounds from the growing fungal isolate prior to noting weed controlling activity. Such a combined application provides a rapid and more consistent weed controlling activity during the period of exposure of a plant to the extract-isolate, or inoculated broth-isolate mixture.

The present invention also contemplates the use of a fungal isolate or any combination of fungal isolates with one or more chemical herbicides. Further, the present invention contemplates biocontrol compositions comprising a fungal isolate of the present invention, or a plurality of fungal isolates with one or more chemical herbicides and a growth medium for supporting the viability of the fungal isolates. The present invention also encompasses the use of a fungal isolate or any combination of fungal isolates with one or more non-*Phoma* fungal strains. Further, the present invention contemplates biocontrol compositions comprising a fungal isolate of the present invention, or a plurality of non-*Phoma* fungal isolates with one or more herbicides and a growth medium for supporting the viability of the fungal isolates.

The above description is not intended to limit the claimed invention in any manner, Furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

EXAMPLES

Example 1

Isolation, Storage and Growth of Fungal Isolates

Fungal Isolates

Fungal strains were isolated from small chlorotic and necrotic lesions on leaf and stem tissues of Canada thistle plants collected from fields, pastures, and roadsides. Purified fungi isolated from the plant tissues were verified to cause the disease symptoms using Koch's postulates.

TABLE 4

Information on fungi isolated from Canada thistle.

| Name | Location | Habitat | Host Growth Stage | Original symptoms |
|---|---|---|---|---|
| 85-24B | Erwood, SK | not recorded | flowering | leaf spots, chlorosis |
| 94-26 | Chatham, ON | roadside | vegetative | chlorosis |
| 94-44B | Melfort, SK | roadside | bolting | chlorosis |
| 94-134 | St. Quentin, NB | waste field | bolting | chlorosis |
| 95-54A1 | Coldbrook, NS | pasture | bolting, flowering | foliar necrosis |
| 97-12B | Valleyview, AB | fallow field | flowering | stem lesion |
| 89-25A | Ituna, SK | field crop | vegetative | leaf spots |
| 94-359A | RM 157, SK | barley field | seed setting | leaf spot, stem lesion |
| 95-268B | Rosthern, SK | filed crop | flowering | leaf spot |
| 97-15B2 | Westlock, AB | pasture | flowering | stem lesion, top dieback |

Isolation of Fungal Isolates

Fungal isolates, obtained as outlined above are surface sterilized for 2 minutes in 0.5% sodium hypochlorite, rinsed in sterile distilled water, and placed on Difco PDA (Potato Dextrose Agar) plates at 24° C. with 12 hours light, for 3-7 days. Fungi growing from the tissues are individually transferred to fresh media and allowed to grow to maturity. Isolates are screened for pathogenicity using Koch's postulates with a detached leaf bioassay. Freshly cut leaves from Canada thistle are surface sterilized and placed on a moist Whatman #3 filter paper in a glass petrie dish. An agar plug from the purified fungal culture is placed on the centre of each leaf, the dish is sealed to prevent moisture loss, and incubated as described above. The development of disease symptoms is observed. Multiple copies of the purified pathogenic cultures are placed in cyropreservation storage as outlined below.

Purified fungal cultures are stored by cryopreservation of spores and mycelia at −78° C. using a 1:1 mixture of 10% skim milk (w/v) to 40% glycerol (v/v) solutions.

The following 10 fungal cultures were identified by CBS, The Netherlands as Phoma cf. macrostoma Montagne, and were deposited within the International Deposit Authority of Canada (IDAC), Bureau of Microbiology, Health Canada, 1015 Arlington Street, Winnipeg, Manitoba, R3E 3R2 Canada as follows:

85-24B (IDAC 230201-1, deposited Feb. 23, 2001);
89-25A (MAC 110401-1, deposited Apr. 11, 2001);
94-26(IDAC 230201-2, deposited Feb. 23, 2001);
94-44B (IDAC 230201-3, deposited Feb. 23, 2001);
94-134(IDAC 230201-4, deposited Feb. 23, 2001);
94-359A (IDAC 110401-2, deposited Apr. 11, 2001);
95-54A1(IDAC 230201-5, deposited Feb. 23, 2001);
95-268B (IDAC 110401-3, deposited Apr. 11, 2001);
97-12B (IDAC 230201-6, deposited Feb. 23, 2001); and
97-15B2(IDAC 110401-4, deposited Apr. 11, 2001).

Culturing and Storing Fungal Isolates

Flasks containing 125 mL of Potato Dextrose Broth (PDB) or V8® juice broth (Dhingra, O.D., and Sinclair, J.B. 1995. Basic Plant Pathology Methods, Second Edition, CRC Press Inc., Boca Raton, Fla. ) were inoculated with $1\times10^5$ conida/L and incubated on a shaker (150 rpm) under ambient room conditions (20° C.) for a minimum of 7-14 days, but more preferably for 14-28 days. The contents of each flask are then vacuum filtered to separate spores and mycelium. Conidial concentration and fresh weight of mycelium are measured.

Fungi may be grown on solid or liquid media. For solid media culture, all fungal isolates are grown on Difco Potato Dextrose Agar (PDA; prepared as per manufacturer's directions) augmented with 3 ml 85% lactic acid per liter of media.

A vial of fungal culture taken from cyropreservation is thawed to room temperature and the contents are aseptically distributed by pouring or pipetting the contents onto three or more prepared plates. The inoculum is spread over the surface of each plate using a sterile glass hockey stick. Agar plates are incubated either on a lab bench at ambient room temperature or in an incubator at 23/18° C. with 12 hours light (20 W cool white fluorescent bulbs) for one to two weeks.

For liquid media culture, 125 ml of Difco PDB is placed in a in a 500 ml Erlenmeyer. The flask is inoculated with either a spore suspension or agar plugs. For the spore suspension, an mature Difco PDA plate is flooded with sterile distilled water and the spores are gently dislodged with a sterile glass hockey stick. The spore suspension is diluted to a concentration of $1\times10^6$ spores/ml and then. 1 ml of the diluted spore solution is added to each flask of liquid medium. To inoculate the liquid medium with agar plugs, 5-8 mm diameter agar plugs are taken from a mature culture on a Difco PDA plate. The inoculated flasks are incubated on a bench top shaker at 150 rpm for 2 weeks at ambient light and temperature conditions.

Mycelia (10 g) from the liquid cultures is placed in 20 mL of 5% skim milk: 20% glycerol cryo-preservation solution and homogenized. The samples are frozen and stored at −18° C. and −73° C. for 30 days and compared to a control prepared immediately after homogenization. Following storage for 30 days, viability is determined by spreading 500 μL of the suspension on a plate of ½ strength PDA, incubating for 4 days, and assessing mycelial growth and conida production. As an example, there was no loss in viability of fungal isolate 85-24B grown in PDB or V8 juice broth after storage at −18° or −73° C. for a period of 1 month.

Example 2

Control of Weed Growth using Fungal Isolates

Effect of Dose on Weed Control

Fungal isolates are grown on PDA and lactic acid for 10 to 14 days. The agar plates cultured with fungus are weighed into doses of 50 g (equivalent to an entire agar plate), 10 g, 5 g, 2.5 g, and 0 g (control), then macerated with sterile distilled water and each dose of the inoculum suspension is brought to a final volume of 50 mL. As an example, 85-24B is tested.

Roots are cut into appropriate lengths, for example roots of Canada thistle are 10 cm long, weighed and placed in 10 cm square pots filled with soil. A dose of the inoculum suspension is poured over the surface of the roots, covered with 1 cm soil, watered to saturation and placed in a greenhouse (20° C. day, 15° C. night; 16 hr daylight) with 6 replicates. Plant are rated for shoot emergence, chlorosis and death at 2, 4, and 6 weeks. At 6 weeks, roots are harvested and weighed. Results from this study using isolate 85-24B are presented in FIG. 1 ( the Rating scale is 1=healthy, dark green foliage; 2=slightly yellow-green foliage; 3=leaves primarily yellow, some yellow-green; 4=leaves primarily white, a few yellow-green; 5=plants completely white; and 6=plants dead).

These results demonstrate that fungal isolates of the present invention can control weed growth, and that this effect is more prominent with increased amounts of inoculum administered to the roots.

Inoculum Mat Bioassay

Roots are washed for 1 hour under running tap water to remove excess soil, and cut into 10 cm lengths each length with at least one bud. The weight of 2-10 cm root lengths, keeping similar root weights for all pots used in a replicate, is recorded A two week old inoculated agar plate is inverted over the root pieces. The control is an agar plate that was not inoculated with a fungus. The agar plate and roots are covered with 2-3 cm of soil mix, and the pots placed in a greenhouse at 20/15° C. and natural light. The total number of shoots or plants, number of shoots or plants that died, total number of shoots or plants with symptoms (i.e. chlorosis, necrosis, lesions) at 2, 4 and 6 weeks after root inoculation is recorded. After six weeks, foliar biomass and root weight were taken. Data analyzed for several parameters:

i) % root growth: [final root weight of treatment/start root weight of treatment]÷[final root weight of control/start root weight of control]×100);

ii) foliar biomass;

iii) shoot emergence as % of control; and iv) % shoots with symptoms.

The effects of several fungal isolates of the present invention on Canada thistle growth and development are shown in Table 5.

TABLE 5

Effect of root inoculation of *Phoma* isolates on disease development of Canada thistle, assayed using inoculum mat bioassay.

| Isolate | Root Zone Application: Chlorosis (scale 1-6)[z] | Foliar fresh wt (g) | RW (% of control)* |
|---|---|---|---|
| Experiment A | | | |
| Control | 1a[y] | 0.67 a | 100 a |
| 95-54A1 | 5 b | 0.24 b | 66 a |
| Experiment B | | | |
| Control | 1 a | 2.6 a | 100 a |
| 97-12B | 6 b | 0.0 b | 14 b |
| Experiment C | | | |
| Control | 1a | 49.1 a | 100 a |
| 89-25A | 4 c | 17.0 c | 29 c |
| 94-359A | 1a | 44.8 ab | 70 b |
| 97-15B2 | 3 b | 35.8 ab | 47 bc |

*RW—root weight;

[z]Rating scale of increasing chlorosis starting from 1 = green, healthy to 6 = white, dead.

[y]Different letters within a column for each experiment indicate significant differences at $P < 0.05$ using Duncan's Multiple Range Test.

The results in Table 5 demonstrate that the isolates were effective in weed control activity, for example controlling Canada thistle growth and development, when applied to soil.

A) Comparison of Fungal Strains for Canada Thistle Control

Using the inoculum mat bioassay, a range of fungal isolates were tested for weed control activity using Canada thistle as a weed.

The results using the above bioassay, on the effect of several fungal isolates on Canada thistle growth and development are shown in Table 6.

TABLE 6

Comparison of fungal isolates and untreated control for reduction in root weight, foliar biomass, mortality, and expression of disease symptoms in Canada thistle conducted in six greenhouse experiments.

| | Control | 85-24B | 94-26 | 94-44B | 94-134 | 95-54A1 | 97-12B | 89-25A | 95-359A | 95-268B | 97-15B2 |
|---|---|---|---|---|---|---|---|---|---|---|---|
| Root weight (% of control) | | | | | | | | | | | |
| Expt 1 | 100 a* | 41 b | 84 a | 18 b | nt** | nt | 68 ab | 73 a | 85 a | 51 ab | nt |
| Expt 2 | 100 a | 33 cd | 8 d | 11 d | nt | nt | 53 bc | 34 cd | 28 cd | 46 c | nt |

TABLE 6-continued

Comparison of fungal isolates and untreated control for reduction in root weight, foliar biomass, mortality, and expression of disease symptoms in Canada thistle conducted in six greenhouse experiments.

| | Control | 85-24B | 94-26 | 94-44B | 94-134 | 95-54A1 | 97-12B | 89-25A | 95-359A | 95-268B | 97-15B2 |
|---|---|---|---|---|---|---|---|---|---|---|---|
| Expt 3 | 100 a | 23 b | 19 b | 16 b | nt | nt | 37 b | 83 a | 77 a | 23 b | nt |
| Expt 4 | 100 a | 6 b | 10 b | 12 b | 28 b | 8 b | nt | nt | nt | 17 b | 14 b |
| Expt 5 | 100 a | 30 b | 24 b | 26 b | 32 b | 16 b | nt | nt | nt | 42 b | 20 b |
| Expt 6 | 100 a | 13 c | 12 c | 9 c | 17 c | 46 b | nt | nt | nt | 14 c | 17 c |
| Mean | 100 ± 5 | 25 ± 4 | 26 ± 6 | 15 ± 2 | 26 ± 5 | 23 ± 8 | 53 ± 11 | 63 ± 11 | 63 ± 10 | 32 ± 6 | 17 ± 4 |
| Foliar fresh wt (g) | | | | | | | | | | | |
| Expt 1 | 5.2 ab | 2.2 c | 5.3 ab | 0.5 d | nt | nt | 4.7 ab | 4.1 b | 4.8 ab | 2.4 c | nt |
| Expt 2 | 4.1 a | 1.4 cde | 0.2 e | 0.1 e | nt | nt | 2.4 bc | 1.7 cde | 0.8 de | 1.8 cd | nt |
| Expt 3 | 3.0 a | 1.1 b | 0.4 b | 0.1 b | nt | nt | 0.9 b | 3.2 a | 2.8 a | 0.6 b | nt |
| Expt 4 | 11.8 a | 0 c | 0 c | 0 c | 4.4 b | 0.2 c | nt | nt | nt | 2.3 bc | 1.4 bc |
| Expt 5 | 8.6 a | 0.7 b | 0.8 b | 2.4 b | 1.6 b | 0.3 b | nt | nt | nt | 3.5 b | 1.1 b |
| Expt 6 | 11.1 a | 0.5 c | 0.8 c | 0.7 c | 0.4 c | 5.9 b | nt | nt | nt | 1.8 c | 1.7 c |
| Mean | 7.2± | 1.0± | 1.3± | 0.6± | 2.1± | 2.2± | 2.7± | 3.0± | 2.8± | 2.0± | 1.4± |
| Mortality (%) | | | | | | | | | | | |
| Expt 1 | 0 | 20 bc | 0 | 38 c | nt | nt | 7 ab | 8 ab | 10 ab | 27 bc | nt |
| Expt 2 | 5 a | 40 b | 95 c | 100 c | nt | nt | 39 b | 50 b | 45 b | 27 ab | nt |
| Expt 3 | 0 | 40 b | 78 c | 85 c | nt | nt | 39 b | 50 b | 45 b | 27 ab | nt |
| Expt 4 | 0 | 92 bc | 100 c | 100 c | 60 b | 92 bc | nt | nt | nt | 88 c | 87 bc |
| Expt 5 | 0 | 72 d | 78 d | 78 d | 40 bc | 90 d | nt | nt | nt | 64 cd | 73 d |
| Expt 6 | 2 a | 84 c | 82 c | 90 c | 77 c | 55 bc | nt | nt | nt | 80 c | 83 c |
| Mean | 1 ± 1 | 57 ± 7 | 72 ± 7 | 80 ± 5 | 59 ± 11 | 79 ± 8 | 39 ± 11 | 23 ± 8 | 18 ± 9 | 58 ± 8 | 81 ± 8 |
| Disease Symptoms (% shoots with chlorosis) | | | | | | | | | | | |
| Expt 1 | 0 | 87 b | 23 a | 100 b | nt | nt | 33 a | 32 a | 20 a | 70 b | nt |
| Expt 2 | 0 | 80 bc | 95 c | 100 c | nt | nt | 70 bc | 50 b | 100 c | 63 b | nt |
| Expt 3 | 0 | 67 b | 90 bc | 100 c | nt | nt | 80 bc | 25 a | 10 a | 85 bc | nt |
| Expt 4 | 0 | 100 c | 100 c | 100 c | 60 b | 96 c | nt | nt | nt | 88 c | 87 c |
| Expt 5 | 0 | 100 c | 88 bc | 78 bc | 73 bc | 100 c | nt | nt | nt | 68 b | 90 bc |
| Expt 6 | 0 | 88 c | 100 c | 100 c | 90 c | 49 b | nt | nt | nt | 80 c | 90 c |
| Mean | 0 ± 0 | 86 ± 6 | 83 ± 6 | 96 ± 2 | 74 ± 9 | 82 ± 8 | 61 ± 11 | 36 ± 10 | 43 ± 13 | 75 ± 7 | 89 ± 6 |

*For each experiment, different letters in a row indicate significant differences among the isolates and the control by Duncan's multiple range test at $P < 0.1$.

**nt—not tested.

These results demonstrate that a range of *Phoma* isolates have a negative impact on root weight, foliar fresh weight, chlorosis, and mortality in Canada thistle, and may be used to control the growth and development of Canada thistle.

The above results were averaged (Table 7). These results indicate that a range of fungal isolates exhibit weed control activity, in that the WCIP is greater than 20%.

TABLE 7

Comparison of 10 fungal strains for control of Canada thistle using the inoculum mat bioassay. Means and standard error calculated from data collected in 3-6 trials, each trial with 5 replicates.

| Treatment | RW* % of control | FFW % of control | Mortality % | IOC % | WCIP % |
|---|---|---|---|---|---|
| Control | 100 ± 5 | 100 ± 4 | 1 ± 1 | 0 ± 0 | 0 |
| 85-24B | 25 ± 4 | 22 ± 6 | 57 ± 7 | 86 ± 6 | 74 |
| 94-26 | 26 ± 6 | 23 ± 7 | 72 ± 7 | 83 ± 6 | 76 |
| 94-44B | 15 ± 2 | 8 ± 3 | 80 ± 5 | 96 ± 2 | 88 |
| 94-134 | 26 ± 5 | 20 ± 8 | 59 ± 11 | 74 ± 9 | 72 |
| 95-54A1 | 23 ± 8 | 20 ± 10 | 79 ± 8 | 82 ± 8 | 79 |
| 97-12B | 53 ± 11 | 59 ± 13 | 39 ± 11 | 61 ± 11 | 47 |
| 89-25A | 63 ± 11 | 76 ± 13 | 23 ± 8 | 36 ± 10 | 30 |
| 94-359A | 63 ± 10 | 69 ± 13 | 18 ± 9 | 43 ± 13 | 32 |
| 95-268B | 32 ± 6 | 31 ± 7 | 58 ± 8 | 75 ± 7 | 68 |
| 97-15B2 | 17 ± 4 | 13 ± 6 | 81 ± 8 | 89 ± 6 | 85 |

*RW—root weight;

FFW—foliar fresh weight;

IOC—incidence of chlorosis;

WCIP—weed control index perennial (WCIP % = {[(100 − root weight) + (100 − foliar fresh weight) + (% mortality) + (% incidence of chlorosis)] ÷ 400} × 100%.)

B) Comparison of Weed Control Activity of Fungal Strains in a Range of Plants

The weed control activity of a range of fungal isolates on several annual and perennial weeds and other plants is examined using the mat bioassay. The plants tested are:

| | |
|---|---|
| Perennial sow thistle | Table 8 |
| Dandelion | Table 9 |
| Scentless chamomile | Table 10(A) |
| Prairie Sunflower | Table 10(B) |
| False Cleavers | Table 11 |
| Wild Oats | Table 12 |
| Green Foxtail | Table 13 |
| Chickweed | Table 14 |
| Wild Buckwheat | Table 15 |
| Field Bindweed | Table 16 |
| Plantain | Table 16A |
| Summary of WCI's | Table 17 |

In Tables 8-17, the following acronyms are used:

RW—root weight;

FFW—foliar fresh weight;

IOC—incidence of chlorosis;

WCIP—weed control index perennial (WCIP %={[(100−root weight)+(100−foliar fresh weight)+(% mortality)+(% incidence of chlorosis)]÷400}×100%.)

WCLA—weed control index annual (WCIA %={[(100−foliar fresh weight)+(% mortality)+(% incidence of chlorosis)]+300}×100%.)

Pooled S.E.=Mean pooled standard error among isolates and control

TABLE 8

Comparison of fungal strains for control of perennial sow thistle.

| Isolate | RW (% of C) | FFW (% of C) | Mortality % | IOC % | WCIP % |
|---|---|---|---|---|---|
| Control (C) | 100 | 100 | 3 | 0 | 0.1 |
| 85-24B | 78 | 100 | 7 | 0 | 7 |
| 94-26 | 67 | 72 | 0 | 33 | 24 |
| 94-44B | 22 | 20 | 33 | 40 | 58 |
| 94-134 | 68 | 100 | 0 | 0 | 8 |
| 95-54A1 | 67 | 100 | 10 | 10 | 13 |
| 97-12B | 57 | 76 | 27 | 40 | 34 |
| 89-25A | 92 | 87 | 20 | 17 | 15 |
| 94-359A | 100 | 98 | 13 | 13 | 6 |
| 95-268B | 100 | 100 | 0 | 0 | 0 |
| 97-15B2 | 72 | 100 | 0 | 0 | 7 |
| Pooled S.E. | 12 | 14 | 4 | 6 | |

TABLE 9

Comparison of fungal strains for control of dandelion.

| Isolate | RW (% of C) | FFW (% of C) | Mortality % | IOC % | WCIP % |
|---|---|---|---|---|---|
| Control (C) | 100 | 100 | 0 | 0 | 0 |
| 85-24B | 55 | 17 | 19 | 100 | 62 |
| 94-26 | 63 | 50 | 12 | 90 | 47 |
| 94-44B | 63 | 24 | 24 | 97 | 59 |
| 94-134 | 88 | 80 | 7 | 21 | 15 |
| 95-54A1 | 47 | 35 | 45 | 80 | 61 |
| 97-12B | 48 | 21 | 35 | 78 | 61 |
| 89-25A | 70 | 31 | 13 | 74 | 43 |
| 94-359A | 73 | 66 | 15 | 38 | 25 |
| 95-268B | 57 | 37 | 10 | 75 | 45 |
| 97-15B2 | 79 | 96 | 4 | 12 | 9 |
| Pooled S.E. | 8 | 13 | 6 | 8 | |

TABLE 10(A)

Comparison of fungal strains for control of scentless chamomile.

| Isolate | FFW (% of C) | Mortality % | IOC % | WCIA % |
|---|---|---|---|---|
| Control (C) | 100 | 12 | 8 | 7 |
| 85-24B | 28 | 83 | 83 | 79 |
| 94-26 | 66 | 27 | 19 | 27 |
| 94-44B | 15 | 86 | 75 | 82 |
| 94-134 | 16 | 83 | 80 | 82 |
| 95-54A1 | 0 | 100 | 94 | 98 |
| 97-12B | 5 | 93 | 91 | 93 |
| 89-25A | 26 | 81 | 60 | 71 |
| 94-359A | 45 | 49 | 46 | 50 |
| 95-268B | 18 | 67 | 67 | 72 |
| 97-15B2 | 14 | 91 | 95 | 91 |
| Pooled S.E. | 15 | 15 | 14 | |

TABLE 10(B)

Comparison of fungal strains for control of Prairie Sunflower.

| Isolate | FFW (% of C) | Mortality % | IOC % | WCIA % |
|---|---|---|---|---|
| Control (C) | 100 | 0 | 0 | 0 |
| 85-24B | 19 | 85 | 88 | 84 |
| 94-26 | nd | 2 | 0 | nd |
| 94-44B | 32 | 65 | 74 | 69 |
| 94-134 | 85 | 0 | 4 | 6 |
| 95-54A1 | 21 | 51 | 86 | 72 |
| 97-12B | 100 | 11 | 15 | 9 |
| 89-25A | 27 | 62 | 75 | 70 |

TABLE 10(B)-continued

Comparison of fungal strains for control of Prairie Sunflower.

| Isolate | FFW (% of C) | Mortality % | IOC % | WCIA % |
|---|---|---|---|---|
| 94-359A | 100 | 0 | 8 | 3 |
| 95-268B | 100 | 0 | 0 | 0 |
| 97-15B2 | 44 | 60 | 44 | 53 |
| Pooled S.E. | 15 | 10 | 10 | |

TABLE 11

Comparison of fungal strains for control of false cleavers.

| Isolate | FFW (% of C) | Mortality % | IOC % | WCIA % |
|---|---|---|---|---|
| Control (C) | 100 | 12 | 0 | 4 |
| 85-24B | 66 | 33 | 24 | 30 |
| 94-26 | 43 | 45 | 42 | 48 |
| 94-44B | 35 | 65 | 63 | 64 |
| 94-134 | 42 | 63 | 40 | 54 |
| 95-54A1 | 41 | 78 | 76 | 71 |
| 97-12B | 48 | 45 | 31 | 43 |
| 89-25A | 97 | 23 | 13 | 13 |
| 94-359A | 90 | 29 | 14 | 18 |
| 95-268B | 6 | 93 | 89 | 92 |
| 97-15B2 | 29 | 72 | 74 | 72 |
| Pooled S.E. | 16 | 10 | 11 | |

TABLE 12

Comparison of fungal strains for control of wild oats.

| Isolate | FFW (% of C) | Mortality % | IOC % | WCIA % |
|---|---|---|---|---|
| Control (C) | 100 | 0 | 0 | 0 |
| 85-24B | 100 | 0 | 0 | 0 |
| 94-26 | na | 4 | 0 | nd |
| 94-44B | 100 | 3 | 61 | 21 |
| 94-134 | 94 | 0 | 0 | 2 |
| 95-54A1 | 100 | 0 | 0 | 0 |
| 97-12B | 100 | 0 | 0 | 0 |
| 89-25A | 100 | 0 | 0 | 0 |
| 94-359A | 100 | 0 | 0 | 0 |
| 95-268B | 96 | 13 | 0 | 17 |
| 97-15B2 | 96 | 0 | 0 | 4 |
| Pooled S.E. | 18 | 1 | 1 | |

TABLE 13

Comparison of fungal strains for control of green foxtail.

| Isolate | FFW (% of C) | Mortality % | IOC % | WCIA % |
|---|---|---|---|---|
| Control (C) | 100 | 3 | 0 | 1 |
| 85-24B | 48 | 37 | 39 | 43 |
| 94-26 | na | 52 | 0 | nd |
| 94-44B | 72 | 0 | 3 | 10 |
| 94-134 | 100 | 0 | 0 | 0 |
| 95-54A1 | 100 | 6 | 0 | 2 |
| 97-12B | 95 | 18 | 0 | 8 |
| 89-25A | 100 | 3 | 0 | 3 |
| 94-359A | 50 | 36 | 43 | 43 |
| 95-268B | 100 | 0 | 0 | 0 |
| 97-15B2 | 100 | 0 | 0 | 0 |
| Pooled S.E. | 20 | 4 | 2 | |

TABLE 14

Effect of fungal isolates on control of chickweed.

| | Emergence % | Chlorosis % | FFW % | Mortality % | WCIA % |
|---|---|---|---|---|---|
| Control (C) | 57 | 0 | 100 | 3 | 0 |
| 85-24B | 55 | 73 | 15 | 70 | 76 |
| 94-134[z] | 65 | 34 | 29 | 70 | 91 |
| 94-26 | 45 | 87 | 1 | 88 | 99 |
| 94-44B | 35 | 100 | 0 | 96 | 59 |
| 95-54A1 | 60 | 73 | 3 | 82 | 84 |
| 97-12B | 36 | 50 | 18 | 40 | 57 |
| 95-268B | 69 | 97 | 2 | 97 | 97 |
| 97-15B2 | 64 | 60 | 22 | 56 | 65 |

[z]Mean of two trials

TABLE 15

Effect of fungal isolates on control of wild buckwheat.

| | Emergence % | Chlorosis % | FFW % | Mortality % | WCIA % |
|---|---|---|---|---|---|
| Control (C) | 54 | 0 | 100 | 0 | 0 |
| 85-24B | 41 | 88 | 1 | 91 | 92 |
| 94-134 | 32 | 87 | 5 | 74 | 39 |
| 94-26 | 40 | 22 | 32 | 28 | 96 |
| 94-44B | 49 | 95 | 1 | 95 | 85 |
| 95-54A1 | 55 | 5 | 78 | 5 | 11 |
| 97-12B | 40 | 4 | 61 | 0 | 15 |
| 89-25A | 39 | 0 | 62 | 0 | 13 |
| 94-359A | 41 | 0 | 49 | 0 | 17 |
| 95-268B | 36 | 89 | 7 | 59 | 81 |
| 97-15B2 | 40 | 63 | 22 | 25 | 55 |

TABLE 16

Effect of fungal isolates on control of field bindweed.

| | Emergence % | Chlorosis % | FFW % | Mortality % | WCIA % |
|---|---|---|---|---|---|
| Control (C) | 34 | 0 | 100 | 9 | 3 |
| 95-54A1 | 33 | 50 | 32 | 43 | 54 |
| 94-359A | 37 | 0 | 75 | 13 | 13 |

TABLE 16A

Effect of fungal isolates on control of plantain (*Plantago lanceolata*).

| | % Emergence | % Chlorosis | % Fresh weight | % Mortality | Weed control index % |
|---|---|---|---|---|---|
| No fungus | 100 | 0 | 100 | 0 | 0 |
| 85-24B | 91 | 98 | 0 | 100 | 100 |
| 94-134 | 96 | 100 | 0 | 98 | 98 |
| 94-26 | 100 | 100 | 0 | 100 | 100 |
| 94-44B | 100 | 100 | 0 | 100 | 100 |
| 95-54A1 | 100 | 100 | 0 | 100 | 100 |
| 97-15B2 | 95 | 25 | 44 | 26 | 36 |

Annual weed control index % = [(100 − foliar fresh weight) + (% mortality) + (% incidence of chlorosis)] ÷ 300 × 100%. A weed control index greater than 25% was considered to be acceptable.

TABLE 17

Weed control index (WCI) of fungal isolates on scentless chamomile, false cleavers, wild oats, green foxtail, chickweed, wild buckwheat, field bindweed, plantain, perennial sow thistle, dandelion, and Canada thistle. A weed control index greater than 25% was considered to be acceptable.

| | Weed control index % | | | | | | | | | | | Summary of Bioactivity Levels: Preferred | Summary of Bioactivity Levels: Most preferred |
|---|---|---|---|---|---|---|---|---|---|---|---|---|---|
| Isolate | SC | FC | WO | GF | CH | WB | FB | PL | PST | DA | CT | WCI: 50-75% | WCI: 75-100% |
| No fungus | 7 | 4 | 0 | 1 | 0 | 0 | 3 | 0 | 0.1 | 0 | 0 | na | na |
| 85-24B | 79 | 30 | 0 | 43 | 76 | 92 | nd | 100 | 7 | 62 | 74 | DA, CT | SC, CH, WB, PL |
| 94-26 | 27 | 48 | nd | nd | 91 | 39 | nd | 100 | 24 | 47 | 76 | none | CH, CT, PL |
| 94-44B | 82 | 64 | 21 | 10 | 99 | 96 | nd | 100 | 58 | 59 | 88 | FC, PST, DA | SC, CH, WB, CT, PL |
| 94-134 | 82 | 54 | 2 | 0 | 59 | 85 | nd | 98 | 8 | 15 | 72 | FC, CH, CT | SC, WB, PL |
| 95-54A1 | 98 | 71 | 0 | 2 | 84 | 11 | 54 | 100 | 13 | 61 | 79 | FC, FB, DA | SC, CH, CT, PL |
| 97-12B | 93 | 43 | 0 | 8 | 57 | 15 | nd | nd | 34 | 61 | 47 | CH, DA | SC |
| 89-25A | 71 | 13 | 0 | 3 | nd | 13 | nd | nd | 15 | 43 | 30 | SC | none |
| 94-359A | 50 | 18 | 0 | 43 | nd | 17 | 13 | nd | 6 | 25 | 32 | SC | none |
| 95-268B | 72 | 92 | 17 | 0 | 97 | 81 | nd | nd | 0 | 45 | 68 | SC, CT | FC, CH, WB |
| 97-15B2 | 91 | 72 | 4 | 0 | 65 | 55 | nd | 36 | 7 | 9 | 85 | FC, CH, WB, SF | SC, CT |

nd = no data;

na = not applicable

Annual weeds: SC = scentless chamomile, WO = wild oats, GF = green foxtail, FC = false cleavers, CH = chickweed, WB = wild buckwheat, FB = field bindweed, PL = plantain seed Annual weed control index % = [(100 − foliar fresh weight) + (% mortality) + (% incidence of chlorosis)] ÷ 300 × 100%

Perennial weeds: PST = perennial sow thistle, DA = dandelion, CT = Canada thistle Perennial weed control index % = [(100 − root weight) + (100 − foliar fresh weigh) + (% mortality) + (% incidence of chlorosis)} ÷ 400 × 100%

Collectively these results demonstrate that a range of *Phoma* macrostoma isolates are effective at selectively controlling weed growth. These isolates are effective at controlling weed growth of broadleaf weeds, including the Plantaginaceae, for example, plantain, the Compositae, for example scentless chamomile, dandelion, perennial sow thistle, false cleavers, and Canada thistle, Caryophyllaceae, for example chickweed, Polygonaceae, for example field bindweed, Convolvulacease, for example field bindweed. *Phoma macrostoma* does not exhibit weed control activity of grassy weeds, for example wild oats, and green foxtail, and can therefore be used to control broad leaf weeds in grasses.

Example 3

Characterization of Weed Control Activity

Hulless Barley Bioassay

To prepare the barley for inoculation with a fungal isolate, soak hulless barley, for example but not limited to, barley cv. CDC Silky in distilled water. Drain off excess water and autoclave for 45 minutes at 121° C. for a total of three times. After autoclaving inoculate the flasks when they are cool.

To prepare the inoculum suspension, a two-week old agar culture plate is placed in a wide mouth bottle with sterile distilled water, and an antibiotic stock solution (streptomycin and vancomycin) is added and the agar antibiotic mixture is homogenized.

Inoculate each container of sterile barley grains with the homogenized inoculum suspension and incubate for two weeks under ambient lab conditions. After incubation, remove barley from container and spread infected grains in a thin layer over the tray to dry for 4 days under ambient room conditions. The dry grains are ground with a mill (i.e. Arthur H. Thomas Co.). The ground inoculum may be stored for up to 3 months at room temperature or refrigerate for longer storage time. The control consists of uninoculated sterile grain treated in the same manner. Viability of ground inoculum is determined by plating 25 pieces on PDA plate and recording the number of particles with colony growth after 3 days and the number of colonies that resemble the original fungal isolate or are contaminants after 7 days.

To conduct the bioassay, healthy roots -are cut into 10 cm long segments, making sure that each root segment has at least one bud. Washed root segments are weighed and placed two per pot. Sprinkle ground inoculum evenly over roots and soil surface, for example about 5 g (other doses may also be used), cover with 2-3 cm of soil mix, and the pots are placed in a greenhouse. The total number of shoots, number of shoots or plants that died, total number of shoots or plants with symptoms (i.e. chlorosis, necrosis, lesions) at 2, 4 and 6 weeks after root inoculation is recorded. Also at 6 weeks collect, rinse and record fresh weight of roots remaining in pot and the fresh weight of foliar tissue. Data are analyzed for several parameters:

i) % root growth (i.e.[final root weight of treatrnent/start root weight of treatment]÷[final root weight of control/start root weight of control]×100);

ii) foliar biomass;

iii) shoot emergence as % of control; and iv) % shoots with symptoms.

A) Duration of Application

To determine the efficacy of a single application of fungal isolates of the present invention over subsequent years, sample fungal isolates were applied to the soil (hulless barley inoculum prepared as outlined above) at a rate of 1 kg/m$^2$ (over a range of particle sizes from 50-840μ; see Table20 below), at three different periods within the growth season: late spring (at the time of emergence of Canada thistle); mid summer; and in the fall. The number of Canada thistle remaining in the test plots were determined over two growth seasons. The results of this experiment are presented in Table 18.

TABLE 18

The effect of a single application of isolate 85-24B to the soil on the emergence of Canada thistle plants in the field.

| | Number of Canada thistle plants per plot over time | | | | |
|---|---|---|---|---|---|
| Treatment | August '99 | September '99 | May '00 | June '00 | July '00 |
| Control | 45 ± 9 | 80 ± 12 | 43 ± 5 | 69 ± 6 | 114 ± 5 |
| Applied June 1999 | 21 ± 1 | 44 ± 2 | 20 ± 2 | 42 ± 4 | 73 ± 4 |
| Applied August 1999 | 14 ± 5 | 39 ± 17 | 22 ± 6 | 41 ± 9 | 80 ± 14 |
| Applied October 1999 | na | na | 46 ± 9 | 82 ± 15 | 131 ± 21 |

na = not available

These data illustrate that a single application of a fungal isolate of the present invention is effective at exerting weed control activity over one or more growth seasons. The weed control activity is greatest if the inoculum is applied in the spring or summer, and is reduced if applied in the fall.

Weed Control Activity in Lawns

To determine the efficacy of a single application of fungal isolates of the present invention for weed control in the establishment of lawn from seed or in previously established perennial turf, sample fungal isolates were applied in the spring to the soil (hulless barley inoculum prepared as outlined above) at a rate between 250-1000 g/m$^2$ (over a range of particle sizes from 50-840μ; see Table 20 below). Inoculum, grass seed and weed seed were weighed out prior to setting up the field plots. A turf grass "Overseeding" mixture was applied at 5.7 g per ¼ m$^2$ (200 lb per acre). It contained 40% Perennial Rye (Manhattan III and Calypso II), 25% Kentucky Blue Grass (Quantum Leap and Alene), 15% Chewings Fescue, 10% Creeping Red Fescue, 10% *Poa trivialis* L. From this amount a 10% weed mix was calculated (5% dandelion seed and 5% chickweed seed) to be 0.6 g per ¼ m$^2$. Inoculum isolates were weighed according to the dose applied. Field plot preparation of the seeded grass area consisted of rototilling the soil and then fully packing the seedbed by stepping on a m$^2$ piece of plywood. Areas that were not smooth, were raked and packed again. The ¼ m$^2$ plots were set up in the centre of the packed area. The grass seed, weed seed and inoculum were sprinkled on top and hand raked in two directions. Then 5 m lengths of row cover were placed on top of the plots for a 2 week period and in this time, the plots were watered everyday, just enough to keep the surface moist and not to let the grass seed dry out while germinating. In previously established turf, the ¼ m$^2$ plots were set up in an area where grass had been growing for more than 20 years. Weed seed and the inoculum were sprinkled on surface and hand raked in two directions. The plots were watered daily for 2 weeks enough to keep the surface moist, but not enough for the inoculum to run off with the water. The number of dandelion and chickweed plants in the test plots were determined over the growing season. Biomass was measured as fresh weight in grams of the grass. The results of this experiment are presented in Table 18A.

TABLE 18A

Effect of a single application of 85-24B to the soil on the mean emergence of dandelion and chickweed in turf.

| Lawn Treatment | Rate of Application g/m$^2$ | Number of weeds per plot Dandelion | Chickweed | Biomass Fr wt. g |
|---|---|---|---|---|
| Establishing | 0 | 100 | 27 | 86 |
| lawn from seed | 250 | 46 | 8 | 45* |
| | 500 | 32 | 7 | 71 |
| | 1000 | 16 | 8 | 135 |
| LSD (0.05) | | 22 | 7 | 64 |
| Previously | 0 | 126 | 20 | 35 |
| established lawn | 250 | 47 | nd | 55 |
| | 500 | 21 | nd | 62 |
| | 1000 | 9 | 10 | 63 |
| LSD (0.05) | | 14 | 7 | 29 |

*large variance due to rabbits and geese feeding on grass in plots

These results demonstrate the control of dandelion and chickweed in lawn establishment and in established lawns. They also show the use of 85-24B for enhancing the growth of grass.

B) Soil Moisture and Air Temperature

Further studies examine the effect of soil moisture and temperature on weed control activity of several fungal isolates, using hulless barley as the inoculum (see above). For these experiments three soil moisture conditions (saturation, field capacity and permanent wilting point), along with 20° or 30° C. days, were considered. The results of these experiments are present in Table 19.

TABLE 19

Effect of temperature and soil moisture on the weed control activity of several fungal isolates (89-25A, 94-26, 94-359A, and 97-12B) of the present invention on Canada thistle.

| Temperature regime ° C. | Soil moisture conditions | Root weight (% of control) Trial 1 | Trial 2 |
|---|---|---|---|
| 30 day/10 night | Saturation | 22 a$^z$ | 31 a |
| | Field capacity | 48 b | 38 a |
| | Permanent wilting point | 100 c | 59 b |
| 20 day/10 night | Saturation | 36 a | 29 a |
| | Field capacity | 31 a | 35 a |
| | Permanent wilting point | 46 a | 66 b |

$^z$For each temperature regime, lower case letters indicate differences among soil moisture conditions averaged over four isolates.

These results illustrate that better weed control activity is obtained with higher soil moisture at either temperature.

C) Application Methods

Methods for the application of the fungal isolates were also examined. This study considered weed control activity as a result of applying a hulless barley inoculum, or a liquid inoculum. For hulless barley, the particle size and dose response of the infected barley were examined (Table 20). For liquid inoculum, the effect of mycelial homogenates (mixed with two composts, dairy, or hog and poultry compost) on weed control activity were examined (Table 21).

Autoclaved barley was used for the preparation of a fungal inoculum as described above. Inoculated sterile barley grains are incubated for two weeks under ambient lab conditions, dried and ground with a mill (i.e. Arthur H. Thomas Co.). The control consists of uninoculated sterile grain treated in the same manner. Viability of ground inoculum is determined by plating 25 pieces on PDA plate and recording the number of particles with colony growth after 3 days and the number of colonies that resemble the original fungal isolate or are contaminants after 7 days.

To conduct the bioassay, healthy roots are cut into 10 cm long segments, making sure that each root segment has at least one bud. Washed root segments are weighed and placed two per pot. Sprinkle ground inoculum evenly over roots and soil surface, for example about 5 g (other doses may also be used), cover with 2-3 cm of soil mix, and the pots are placed in a greenhouse. The change in root weight at 6 weeks after root inoculation is recorded. The results are presented in Table 20.

TABLE 20

The effect of granule size and application dose on the efficacy of 85-24B to reduce root weight of Canada thistle.

| Granule size$^z$ (μ) | Application dose (g/m$^{2)}$ | Root weight (% of control) |
|---|---|---|
| >840 | 100 | 82 |
| | 500 | 55$^y$ |
| | 1000 | 25 |
| 840-590 | 100 | 98 |
| | 500 | 74 |
| | 1000 | 6 |
| 590-49 | 100 | 45 |
| | 500 | 46 |
| | 1000 | 2 |
| Mean Pooled Standard Error | | 18 |

$^z$>840 = whole barley seed infested with 85-24B had 100% viability/particle; 840-590 = infested barley seed ground and passed through a 20 mesh, but not a 30 mesh sieve had 75% viability/particle; 590-49 = infested barley seed ground and passed through a 30 mesh sieve had 75% viability/particle.

$^y$Mean of two trials

The results presented in Table 20, demonstrate that a range of barley granule sizes and application rates are effective in controlling weed growth (indicated by reduced root growth). Increased efficacy is observed with smaller sized granules and higher dose application rates.

Compost Bioassay

The fungus is grown in liquid culture as described above (see Culture of fungal isolates, Example 1). Using a double layer of cheesecloth, the liquid is drained by gravitational force from the mycelium. A ratio of about 1:3.2 (v/v) mycelium to water is homogenized to produce about $10^5$ to $10^6$ cfu/mL. The homogenate was mixed with composted manure in a ratio of about 1:2 (v/v).

Two segments of weed root, for example, about 10 cm for Canada thistle roots, are placed in a pot that is three quarters full with soil mix (3 sandy loam: 1 sphagnum peat moss: 1 medium grade vermiculite: 1 wash screened 9 mm sand) and packed firmly. Root segments are weighed and placed two per pot. The treated compost (compost-homogenate mix) is placed in the pot and then covered with additional soil mix before watering thoroughly. Pots are placed in a greenhouse, and the total number of shoots/pot, total number of shoots or plants with symptoms (i.e. chlorosis, necrosis, lesions) at 2, 4 and 6 weeks is recorded. Also at 6 weeks roots are collected, rinsed, and the fresh weight recorded, as is the fresh weight of foliar tissue. The data are analyzed for several parameters:

i) % root growth (i.e. [final root weight of treatment/start root weight of treatment]÷[final root weight of control/start root weight of control]×100); and ii) foliar biomass.

The results are presented in Table 21 (A).

TABLE 21(A)

Effect of using mycelial homogenate of 85-24B to inoculate composted manure for the control of Canada thistle.

| Compost | Treatment | Root weight % of control | Foliar fresh weight % of control |
|---|---|---|---|
| Dairy | No fungus | 100 a | 100 a |
| | Fungus | 65 b | 76 a |
| Hog and Poultry | No fungus | 100 a | 100 a |
| | Fungus | 28 c | 49 c |

These results demonstrate that liquid inoculum prepared as a homegenate using a variety of compost media, is effective in controlling weed growth.

Soil Drench Bioassay

The fungal isolates grown in liquid culture as described above (see Culture of fungal isolates, Example 1). One treatment used a mixture of 94-359A, 94-44B, and 85-24B grown for about 4-8 weeks and the other treatment used 85-24B grown for 2 weeks. The mycelium and liquid culture broth were homogenized to produce about $10^3$ to $10^4$ cfu/mL. The control was uninoculated liquid culture medium. Twenty-five dandelion seeds were sown 6 mm deep in 100 mL soilless planting mix (equivalent to 0.02 $m^2$) and 100 mL of homogenate was poured on the soil. Counts were made of the number of dandelion seedlings that emerged and the number of chlorotic seedlings after 5, 7, and 14 days. The results are presented in Table 21(B).

TABLE 21(B)

The effect of mycelial homogenates of fungal isolates applied as soil drench for the control of dandelion.

| Treatment | Culture Period | Mean cfu/mL | % Chlorosis 5 days | % Chlorosis 7 days | % Chlorosis 14 days |
|---|---|---|---|---|---|
| Control | 2 weeks | 0 | 0 | 0 | 0 |
| Fungal mixture | 4-8 weeks | $10^3$ | 100 | 100 | 100 |
| 85-24B | 2 weeks | $10^4$ | 0 | 50 | 75 |

These results demonstrate that fungal homogenates with about $10^3$ to $10^4$ cfu/mL may be applied as a soil drench at the rate of about 5 L/$m^2$ for weed control activity, and that faster and greater weed control activity is obtained with mixtures of aged inoculum.

Seed Treatment Bioassay

Isolate 94-44B was grown in liquid culture for 4 weeks as described above (See Culture of fungal isolates, Example 1). The mycelium and liquid culture broth were homogenized to produce about $10^3$ to $10^4$ cfu/mL. The fungal homogenate ( 1 mL) and 1 mL of 2% methocil (a cellulose sticker) was used to coat 36 seeds of Katewpa wheat (138 cfu/seed) or 173 seeds of creeping red fescue grass seed (29 cfu/seed) in a glass Petrie dish. The coated seed was air dried overnight in a laminar flow hood. The wheat seeds and 20 dandelion seeds were planted in a 4 inch pot with soil-less planting medium and watered thoroughly. The % of dandelion plants with chlorosis and the fresh weight biomass of wheat were recorded 14 days later. See Table 21(C).

TABLE 21(C)

The effect of treating the seed of a crop with fungal isolate 94-44B on the control of dandelion and on crop growth.

| Treatment | No. of chlorotic dandelions % | Crop Biomass (% of untreated control) |
|---|---|---|
| Grass seed - treated | 6 | 116 |
| Grass seed - untreated | 0 | 100 |
| Wheat seed - treated | 23* | 122* |
| Wheat seed - untreated | 0 | 100 |

*significantly different than the untreated control at $P < 0.05$

These results demonstrate that the inventive fungal isolate may control dandelions by seed treatment of crops. It also demonstrates a dose effect such that larger seeds with more cfu/seed gave greater control than smaller seeds with fewer cfu/seed.

Pre- and Post-Emergence Foliar Spray Applications

Isolate 94-44B was grown in liquid culture for four weeks as described above (See Culture of fungal isolates, Example 1). The liquid culture was filtered through a nylon mesh cloth and the liquid culture broth and the mycelial fractions were saved separately. A 150 ml aliquot of the liquid culture broth was filtered through a 0.45 um cellulose acetate filter to produce the filtered culture broth treatment. Another 150 ml aliquot of the liquid culture broth had 15% mycelium (w/v) added to it and was then homogenized to produce the treatment called the unfiltered liquid culture broth containing $10^6$ to $10^7$ propagules/ml. (Propagules comprised both mycelial fragments and spores). These two treatments plus a water control were sprayed onto 6-4 inch pots using a track sprayer at a rate of 480 L/ha. Each pot was seeded with 0.11 g of grass cv. Overseeding Mixture and 20 dandelion seeds in a soiless planting medium. Pots were sprayed 1-2 days after seeding as a pre-emergent foliar spray application. Pots were also sprayed two weeks after seeding as a post-emergence foliar spray application. Three weeks after spraying, the following data were recorded: total number of dandelions per pot, number of chlorotic dandelions per pot, fresh weight of grass per pot in grams, fresh weight of dandelion per pot in grams. See Table 21(D).

TABLE 21(D)

The effect of pre- and post-emergent spray applications of liquid culture broths of isolate 94-44B.

| Time of Application | Spray Treatment | Fresh weight (as % water control) Grass | Fresh weight (as % water control) dandelion | Number of dandelions Chlorotic (%) | Number of dandelions Total |
|---|---|---|---|---|---|
| Pre-emergent | Filtered culture broth | 123 b | 16 c | 38 c | 5 b |
| | Unfiltered culture broth | 159 a | 31 bc | 56 b | 7 ab |
| | Water Control | 100 b | 100 a | 0 a | 10 a |

TABLE 21(D)-continued

The effect of pre- and post-emergent spray applications of liquid culture broths of isolate 94-44B.

| Time of Application | Spray Treatment | Fresh weight (as % water control) Grass | dandelion | Number of dandelions Chlorotic (%) | Total |
|---|---|---|---|---|---|
| Post-emergent | Filtered culture broth | 113 a | 20 b | 89 b | 5 a |
| | Unfiltered culture broth | 93 a | 41 b | 86 b | 8 a |
| | Water Control | 100 a | 100 a | 0 a | 7 a |

Different lowercase letters within a column for each application time indicate significant differences at P < 0.05.

These results demonstrate that the inventive fungal isolate may control dandelion by spray application methods either before or after plant emergence and improve the growth of grass by pre-emergent spray application.

Example 4

Effect of Fungal Isolates of the Present Invention on Agriculturally Important Plants Effect of Methods of Application A) Inoculum Mat Bioassay A range of agriculturally important plants were tested to determine the host specificity of the fungal isolates of the present invention. The fungal isolates were applied to oilseed, cereal, pulse, and forage crops using the inoculum mat bioassay outlined in Example 2. The effect of these fungal isolates on germination, chlorosis, foliar fresh weight, and mortality were examined.

Crops for Host Range Testing

Sensitivity of crops to the fungal isolates was tested using the inoculum mat bioassay (see Example 2), using high inoculum loads. Therefore, the results show more susceptible reactions than would occur under more natural conditions of infection.

Crops and cultivars tested were as follows:

1) Cereal and Other Monocots

Wheat—cvs. Katepwa, AC Domain, AC Karma, Biggar, Kyle

Barley—cvs. Harrington, Silky

Oat—cvs. Derby or Walden

Millet—cvs. Minco or Prairie Gold

Canary seed—cv. Keet

2) Oilseed Crops

Canola—cvs. AC Excel, AC Parkland

Mustard—cvs. Cutlas, Ochre

Flax—cv. Vimy

Sunflower—cvs. Cargill SF270 or IS7111

Safflower—cv. Lethbridge

3) Pulse Crops

Lentil—cvs. Laird, Eston

Field pea—cv. Express

Chickpea—cv. Sanford

Faba bean—cv. CDC Fatima

4) Forage Crops

Clovers—yellow clover cv. Norgold, white clover cvs. Polara and Sonja, common clover, red clover cvs. Altaswede or Florex Birdsfoot trefoil—cv. Cree Alfalfa—cv. Beaver The results of these experiments are present in Table 22 (effect on germination and chlorosis) and Table 23 (effect on foliar fresh weight and mortality).

TABLE 22

The effect of fungal isolates on agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Germination | | | | | | | | | | | |
| Wheat | 5 | — | — | — | — | — | — | — | — | — | — |
| Barley | 2 | — | +a | — | — | — | — | — | — | — | — |
| Oat | 1 | — | — | — | — | — | — | — | — | — | — |
| Millet | 1 | — | — | — | — | — | — | — | — | — | +a |
| Canary Seed | 1 | — | — | — | — | — | — | — | — | — | — |
| Canola | 2 | — | — | — | — | +a | — | — | — | — | +b |
| Mustard | 2 | +a | — | — | — | +b | +a | +a | +a | — | +b |
| Flax | 1 | — | — | — | — | — | — | — | — | — | +a |
| Sunflower | 1 | — | — | — | — | — | — | — | — | — | — |
| Safflower | 1 | — | — | — | — | — | — | — | — | — | — |
| Lentil | 2 | — | — | +a | +a | — | — | — | — | — | — |
| Field Pea | 1 | — | — | — | — | — | — | — | — | — | — |
| Chickpea | 1 | — | — | — | — | +a | — | — | — | — | — |
| Faba bean | 1 | — | — | — | — | — | — | — | — | — | — |
| Clovers | 5 | — | — | +a | — | — | +b | +a | +b | +b | — |
| Birdsfoot trefoil | 1 | +a | — | — | — | — | +a | +a | +a | — | +a |
| Alfalfa | 1 | — | — | +a | — | — | — | — | — | — | — |

TABLE 22-continued

The effect of fungal isolates on agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Chlorosis | | | | | | | | | | | |
| Wheat | 5 | — | — | — | — | — | — | — | — | — | — |
| Barley | 2 | — | — | — | — | — | — | — | — | — | — |
| Oat | 1 | — | — | — | — | — | — | — | — | — | — |
| Millet | 1 | — | — | — | — | — | — | +a | — | — | +a |
| Canary seed | 1 | — | — | — | — | — | — | — | — | — | — |
| Canola | 2 | +b | — | +b | +a | +b | +b | +b | — | +b | — |
| Mustard | 2 | +b | — | +b | — | +b | +b | +b | +a | +b | — |
| Flax | 1 | +a | — | — | — | — | — | +a | — | — | — |
| Sunflower | 1 | +a | — | +a | — | +a | — | +a | — | — | — |
| Safflower | 1 | +a | — | +a | — | +a | — | — | — | — | +a |
| Lentil | 2 | +b | +b | +b | +a | +b | — | +a | +a | — | +a |
| Field pea | 1 | +a | +a | +a | — | +a | — | — | — | — | +a |
| Chickpea | 1 | +a | — | +a | — | +a | — | — | — | — | +a |
| Faba bean | 1 | +a | +a | +a | — | +a | — | — | — | — | +a |
| Clovers | 5 | +d | — | +c | — | +c | +b | +c | +c | +b | +c |
| Birdsfoot trefoil | 1 | +a | — | +a | — | — | — | +a | +a | +a | +a |
| Alfalfa | 1 | + | +a | +a | — | +a | +a | +a | — | +a | +a |

+indicates a detrimental effect on at least one or more cultivars tested for each crop using ANOVA to compare treatment and control at P = 0.05;
— indicates no detrimental response to the treatment using ANOVA to compare treatment and control at P = 0.05

TABLE 23

The effect of fungal isolates on agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Foliar Fresh Weight | | | | | | | | | | | |
| Wheat | 5 | +a | na | — | +a | +a | — | — | — | — | — |
| Barley | 2 | — | na | — | — | — | — | — | +a | — | — |
| Oat | 1 | +a | na | — | — | — | — | — | — | — | — |
| Millet | 1 | — | na | — | — | +a | — | +a | — | — | +a |
| Canary seed | 1 | — | na | — | — | — | — | — | — | — | — |
| Canola | 2 | +a | na | — | +a | +b | +a | +b | +b | +b | +b |
| Mustard | 2 | +a | na | — | — | +b | +b | +a | +a | +a | +b |
| Flax | 1 | +a | na | — | — | +a | — | — | — | — | +a |
| Sunflower | 1 | na | na | na | na | +a | — | — | na | na | na |
| Safflower | 1 | +a | na | — | — | — | — | — | — | — | +a |
| Lentil | 2 | +b | na | +b | +a | +a | +a | +a | +b | — | +b |
| Field pea | 1 | +a | na | — | — | +a | — | — | — | — | +a |
| Chickpea | 1 | — | na | +a | — | — | +a | — | +a | — | +a |
| Faba bean | 1 | +a | na | — | — | +a | — | — | — | — | +a |
| Clovers | 5 | +b | na | +b | — | +b | +b | +a | +b | +c | +c |
| Birdsfoot trefoil | 1 | +a | na | +a | — | — | — | +a | +a | +a | +a |
| Alfalfa | 1 | +a | +a | +a | — | +a | +a | +a | — | +a | +a |
| Mortality | | | | | | | | | | | |
| Wheat | 5 | — | — | — | — | — | — | — | — | — | — |
| Barley | 2 | — | — | — | — | — | — | — | — | — | — |
| Oat | 1 | — | — | — | — | — | — | — | — | — | — |
| Millet | 1 | — | +a | — | — | — | — | — | — | — | +a |
| Canary seed | 1 | — | — | — | — | — | — | — | — | — | — |
| Canola | 2 | +b | +a | +b | +a | +b | +b | +b | — | +b | +b |
| Mustard | 2 | +b | — | +b | — | +b | +b | +b | +a | +b | +b |
| Flax | 1 | +a | — | — | — | — | — | — | — | — | +a |
| Sunflower | 1 | +a | — | na | na | +a | — | +a | na | na | na |
| Safflower | 1 | +a | — | +a | — | +a | — | — | | — | +a |
| Lentil | 2 | +b | +a | +b | — | +b | — | — | — | — | — |
| Field pea | 1 | +a | — | +a | — | +a | — | — | — | — | — |
| Chickpea | 1 | — | — | +a | — | +a | — | — | — | — | — |
| Faba bean | 1 | — | — | +a | — | — | — | — | — | — | — |

TABLE 23-continued

The effect of fungal isolates on agriculturally important plants. The plus symbol indicates a detrimental effect to one or more cultivars tested and the letter indicates the number of cultivars affected (a = 1; b = 2; c = 3; d = 4; e = 5).

| Crop | No. of cultivars | 85-24B | 94-26 | 94-44B | 94-134 | 95-54A1 | 97-12B | 89-25A | 94-359A | 95-268B | 97-15B2 |
|---|---|---|---|---|---|---|---|---|---|---|---|
| Clovers | 5 | +e | — | +a | +a | +b | +a | +c | +a | +d | +d |
| Birdsfoot trefoil | 1 | +a | — | +a | — | — | — | +a | — | +a | +a |
| Alfalfa | 1 | +a | +a | +a | — | +a | +a | +a | — | +a | +a |

+indicates a detrimental effect on at least one or more cultivars tested for each crop using ANOVA to compare treatment and control at P = 0.05;
— indicates no detrimental response to the treatment using ANOVA to compare treatment and control at P = 0.05

The results presented in Tables 22 and 23 demonstrate that many plant cultivars of important agricultural species are not affected by fungal isolates of the present invention when applied at high inoculum loads, and that these isolates may be used as a bioherbicide to control weed activity in the presence of crops. Lower inoculum loads, that are effective in exhibiting weed control activity but not harmful to crop plants, may be used to minimize the impact on agriculutral plants if desired.

B) Hulless Barley Inoculum

To determine the residual effects of a single application of fungal isolates of the present invention on agriculturally important crops grown in the field, sample fungal isolates were applied to the soil using the hulless barley inoculum at 1 $kg/m^2$ at three different periods within the growth season to control Canada thistle (See Example 3, Duration of Application). Lentil seed of the cultivar Laird was sown into the treated and control areas at the rate of 70-80 kg/ha approximately 10-14 months after the time of bioherbicide application. The number of lentil plants emerged per plot and the number of plants with chlorosis were counted. The results of this experiment are presented in Table 24(A). The data of a similar experiment, on Canada thistle, is presented in Table 18.

TABLE 24 (A)

The effect of residual fungal inoculum of 85-24B applied to the soil on the mean emergence of lentil per plot and mean number of lentil plants with chlorosis per plot.

| Treatment | Emergence | Chlorosis |
|---|---|---|
| Control | 38 ± 12 S.E. | 0 |
| Applied: | | |
| June 1999 | 46 ± 1 | 1.5 |
| August 1999 | 40 ± 13 | 0 |
| October 1999 | 19 ± 30.3 | |

These results demonstrate that fungal isolates in the present invention do not have harmful residual activity to agriculturally important field crops when applied at high rates of field application in the spring and summer under natural conditions of infection.

Example 5

Phytotoxin Production

The weed control activity of heat killed fungal isolates was examined. Hulless barley inoculum was heat killed and applied to Canada thistle or the heat-killed innoculum was mixed with grass seed contaminated with 5% dandelion seed as described below (Tables 24 (B) and 24(C)). The results indicate that heat killed fungal isolates retain weed control activity. Therefore, the effect of filtered inoculated broth or extracts of fungal isolates of the present invention on weed growth was also examined (Table 25).

Weed Control by the Fungal Agent or by Metabolites Produced by the Fungal Agent

Hulless barley grains inoculum is prepared as outlined above (Example 3). The barley inoculum is autoclaved and applied to soil in which Canada thistle is grown or the inoculum is mixed with grass seed contaminated with 5% dandelion seed (see above Example 3). As a control, regular barley grain or non-infested barley inoculum are applied to the soil. These results were repeated under greenhouse and field conditions. The results of the experiments are shown in Table 24B and Table 24C.

TABLE 24(B)

The effect of heat-killed fungal-infested barley grains on Canada thistle.

| Treatment | Chlorosis | Root weight % of control | Mortality % |
|---|---|---|---|
| Fungal Isolate 89-25A | | | |
| Untreated control | no | 100 a | 0 |
| Infested grain | yes | 9 b | 70 c |
| Autoclaved grain | yes | 33 b | 20 ab |
| Fungal Isolate 97-12B | | | |
| Untreated control | no | 100 a | 0 |
| Infested grain | yes | 67 ab | 30 b |
| Autoclaved grain | yes | 55 ab | 17 ab |

Different letters within a column indicate significant differences at P < 0.05 using Duncans multiple range test. Fungal viability of infested grain was 100% while the viability in the autoclaved sample was 0%.

These experiments demonstrate that heat killed fungal inoculum exhibits weed control activity, and that live fungal inoculum is not required for weed control activity. These results suggest that a natural product is made by fungal isolates of the present invention. Crude extracts of a phytotoxin fraction were obtained and analysed for weed control activity.

TABLE 24C

The effect of heat-killed fungal infested barley grains (isolate 85-24B) on emergence of dandelion in turf.

| Treatment | Average No. dandelion per plot | Biomass of Grass per plot (Fresh wt. g.) |
|---|---|---|
| No grain | 117 | 50 |
| Grain | 48 | 57 |
| Infested grain | 19 | 69 |
| Heat-killed infested grain | 16 | 98 |
| LSD (0.05) | 16 | 29 |

Field test conducted in mid-August and ran for 4 weeks before taking biomass.

These results demonstrate that the fungal agent or metabolites produced by the fungal agent may control dandelion in lawns and that the metabolites may improve the growth of the grass.

Phytotoxin Extraction and Bioassay

Fungal isolates were grown in liquid culture media on a shaker for 4 weeks under ambient light and temperature conditions. The culture was separated into a broth and a mycelium fraction by vacuum filtration using Buchner funnel lined with Whatman #1 filter paper and 24 layers of cheesecloth. The broth fraction (filtered inoculated broth)was reduced to dryness either a using a roto-evaporator (40° C.) or freeze-dryer. The mycelium fraction was placed in the chloroform for 3 hours to overnight then vacuum filtered through Whatman #1 filter paper to separate solvent and mycelium. The filtered solvent was roto-evaporated to dryness. The control was uninoculated liquid culture media treated the same as the broth fraction. The dried extracts were stored in flasks in the refrigerator until used. For testing, the dried extracts from both the broth and mycelium fractions were first dissolved in 2-5 ml of distilled water and then an equal amount of 80% methanol was added to each flask. The control treatment was 40% methanol. Methanol and ethyl acetate extracts were also obtained from the mycelium fraction following the chloroform extraction step, and examined for weed control activity as described below.

A bioassay was used to determine the presence of phytotoxins in droplets of the fractions that caused chlorotic symptoms similar to that caused by the fungus on leaves of a susceptible plant (in this example, faba bean was used as a test plant) or Canada thistle (weed host). Faba bean seeds were planted into soil mix and thinned to 5 plants per pot using 2 pots per treatment. Canada thistle roots were planted in soil mix and after 3 weeks, pots with 2-3 shoots were selected. Two −10 µl drops of an extract were applied to 2 leaves per faba bean plant and 3 leaves per Canada thistle shoot; one droplet over a puncture wound made from an insect pin and the other droplet directly on the leaf surface. Plants were observed daily for 10 days for chlorosis.

A different bioassay was used to determine the impact of the phytotoxins from the fractions on the fresh weight of faba bean. In this assay, faba bean seeds were mixed with 1 ml of extract and 1 ml of 2% methocil to coat the seeds and then left to air dry overnight. Five seeds were planted per pot in soil mix. Plants were rated for emergence and chlorosis after 10 days, and foliar biomass (fresh weight) after 4 weeks.

The weed control activity of these solvent extracts are present in Table 25 (A; chloroform extract) and Table 25 (B;chloroform, methanol or ethyl acetate extracts).

Weed control activity, determined by the percentage of chlorotic plants (faba bean, FB or Canada thistle, CT) observed 10 days after receiving droplets of a chloroform extract obtained from fungal isolate 94-26, is presented in Table 25(A).

TABLE 25(A)

Weed control activity of a solvent extract of a fungal isolate of the present invention. Solvent control is 40% methanol, or the uninoculated broth.

| | % chlorotic plants | | | | | |
|---|---|---|---|---|---|---|
| | Trial 1 | | Trial 2 | | Trial 3 | Trial 4 |
| Treatment | FB | CT | FB | CT | FB | FB |
| Solvent control | 0 | 0 | 0 | 0 | 0 | 0 |
| Uninoculated broth | 0 | 0 | 0 | 0 | 0 | 0 |

TABLE 25(A)-continued

Weed control activity of a solvent extract of a fungal isolate of the present invention. Solvent control is 40% methanol, or the uninoculated broth.

| | % chlorotic plants | | | | | |
|---|---|---|---|---|---|---|
| | Trial 1 | | Trial 2 | | Trial 3 | Trial 4 |
| Treatment | FB | CT | FB | CT | FB | FB |
| Filtered Inoculated broth | 100 | 67 | 90 | 80 | 100 | 100 |
| Mycelium-chlorofom | 100 | 100 | 0 | 0 | 0 | 100 |

treatment n = 10 plants

The weed control activity of chloroform, methanol, or ethyl acetate fractions is also examined. Weed control activity is assayed by monitoring emergence, chlorosis, and foliar fresh weight of faba bean that had seed treated with various solvent extracts from 94-26, or uninoculated control broth. The results of this experiment are present in Table 25(B).

TABLE 25(B)

Weed control activity of various solvent extracts of a fungal isolate of the present invention. Uninoculated broth is a control.

| Treatment | Emergence % | Chlorosis % | Fresh weight g |
|---|---|---|---|
| Uninoculated broth | 93 a | 0 | 36 a |
| Filtered Inoculated broth | 100 a | 100 b | 18 cd |
| Mycelium-chloroform | 100 a | 100 b | 11 d |
| Mycelium-methanol | 87 a | 87 b | 20 bc |
| Mycelium-ethyl acetate | 93 a | 13 a | 37 a |

n = 15 plant;
Different letters within a column indicate significant differences at $P < 0.05$ using a LSD test The results presented in Tables 25 (A) and (B) demonstrate that filtered inoculated broth and solvent extracts obtained from the fungal isolates of the present invention induce disease symptoms, reduce growth, and exhibit weed control activity in susceptible plants. Therefore, filtered inoculated broth, extracts from mycelium, or a combination thereof, may be used to control weed growth.

All references are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method of controlling one or more broad leaf weeds comprising administering mycelia of *Phoma* cf. *macrostoma* isolated from Canada thistle, an extract therefrom, an inoculated broth therefrom, or a combination thereof, to said weeds, or to soil where said weeds grow.

2. The method of claim 1, wherein said one or more broad leaf weeds is a species of a family selected from the group consisting of Compositae, Caryophyllaceae, Convolvulaceae, Plantaginaceae and Rubiaceae.

3. The method of claim 1, wherein said one or more broad leaf weeds is selected from the group consisting of Canada thistle, perennial sowthistle, dandelion, scentless chamomile, false cleavers, chickweed, wild buckwheat, field bindweed, plantain, prairie sunflower, clover and mustard.

4. A biocontrol agent comprising mycelia of one or more than one *Phoma* cf *macrostoma* isolate isolated from Canada thistle, an extract therefrom, an inoculated broth therefrom, or a combination thereof, said biocontrol agent exhibiting weed control activity, growth enhancement activity, or a combination thereof.

5. A biocontrol composition, comprising the biocontrol agent of claim 4, and a medium for supporting viability of said one or more than one *Phoma* isolate.

6. The biocontrol composition of claim 5, wherein said medium is selected from the group consisting of Agar, pesta, peat prill, vermiculite, clay, starches, potato dextrose broth, vegetable juice broth, cereal grain and legume grain.

7. A method of controlling weed development during crop growth comprising:
a) adding an effective amount of said biocontrol agent of claim 4 to produce a treated soil,
b) planting said crops in said treated soil,
c) growing said crop.

8. A method of controlling weed development during crop growth comprising:
a) planting said crop,
b) adding an effective amount of said biocontrol agent of claim 4 to soil where said crop is planted,
c) growing said crop.

9. A method of controlling weed development during crop growth comprising:
a) adding an effective amount of said biocontrol agent of claim 4 to crop seeds, to produce treated crop seed;
b) planting said treated crop seed; and
c) growing said crop.

10. A method of controlling weed development during established crop growth comprising:
a) adding an effective amount of said biocontrol agent of claim 4 to the established crop;
and
b) growing the crop.

11. A method of controlling weed development during crop growth comprising:
a) adding an effective amount of said biocontrol composition of claim 5 to produce a treated soil,
b) planting said crops in said treated soil,
c) growing said crop.

12. A method of controlling weed development during crop growth comprising:
a) planting said crop,
b) adding an effective amount of said biocontrol composition of claim 5 to soil where said crop is planted,
c) growing said crop.

13. A method of controlling weed development during crop growth comprising:
a) adding an effective amount of said biocontrol composition of claim 5 to crop seeds to produce treated crop seed;
b) planting said treated crop seed; and
c) growing said crop.

14. A method of controlling weed development during established crop growth comprising:
a) adding an effective amount of said biocontrol composition of claim 5 to the established crop; and
b) growing the crop.

15. A method of controlling weed development comprising applying the biocontrol agent of claim 4 to soil where said weed grows.

16. The method of claim 15, wherein said biocontrol agent is an extract from said one or more than one *Phoma macrostoma* isolate.

17. A method of controlling weed development comprising applying the biocontrol composition of claim 5 to soil where said weed grows.

18. The method of claim 17, wherein said biocontrol agent is said one or more than one *Phoma macrostoma* isolate.

19. The method of claim 15, wherein said step of applying comprises dusting, rubbing, spreading, drilling, banding, broadcasting, spraying, liquid injection, pouring or soil drenching.

20. The method of claim 17, wherein said step of applying comprises dusting, rubbing, spreading, drilling, banding, broadcasting, spraying, liquid injection, pouring or soil drenching.

21. A method of controlling weed development comprising applying the biocontrol agent of claim 4 to said weed.

22. A method of controlling weed development comprising applying the biocontrol composition of claim 5 to said weed.

23. The method of claim 21, wherein said step of applying comprises dusting, rubbing, spreading, broadcasting, spraying, or pouring.

24. The method of claim 22, wherein said step of applying comprises dusting, rubbing, spreading, broadcasting, spraying, or pouring.

25. The agent of claim 4, wherein said extract is selected from the group consisting of heat killed barley inoculum, a chloroform extract of said *Phoma* isolate, a methanol extract of said *Phoma* isolate, and an ethyl-acetate extract of said *Phoma* isolate.

26. The agent of claim 4, wherein said inoculated broth is selected from the group consisting of a crude inoculated broth, a filtered inoculated broth, a concentrated inoculated broth or a centrifuged inoculated broth.

27. The method of claim 16, wherein said extract is selected from the group consisting of heat killed barley inoculum, a chloroform extract of said *Phoma* isolate, a methanol extract of said *Phoma* isolate, and a ethyl-acetate extract of said *Phoma* isolate.

28. The method of claim 15, wherein said inoculated broth is selected from the group consisting of a crude inoculated broth, a filtered inoculated broth, a concentrated inoculated broth or a centrifuged inoculated broth.

29. A coated crop seed, comprising mycelia of one or more *Phoma* cf. *macrostoma* isolates isolated from Canada thistle and a binder.

30. A coated crop seed, comprising an inoculated broth, or an extract obtained from mycelia of one or more *Phoma* cf. *macrostoma* isolates isolated from Canada thistle, and a binder.

31. The coated crop seed of claim 29, wherein said *Phoma* cf *macrostoma* isolate is selected from the group consisting of:
a) 85-24B (IDAC 230201-1, deposited Feb. 23, 2001),
b) 89-25A (IDAC 110401-1, deposited Apr. 11, 2001),
c) 94-26(IDAC 230201-2, deposited Feb. 23, 2001),
d) 94-44B (IDAC 230201-3, deposited Feb. 23, 2001)
e) 94-134(IDAC 230201-4, deposited Feb. 23, 2001),
f) 94-359A (IDAC 110401-2, deposited Apr. 11, 2001),
g) 95-54A1(IDAC 230201-5, deposited Feb. 23, 2001),
h) 95-268B (IDAC 110401-3, deposited Apr. 11, 2001),
i) 97-12B (IDAC 230201-6, deposited Feb. 23, 2001), and
j) 97-15B2(IDAC 110401-4, deposited Apr. 11, 2001).

32. The coated crop seed of claim 30, wherein said *Phoma* cf. *macrostoma* isolate is selected from the group consisting of:
a) 85-24B (IDAC 230201-1, deposited Feb. 23, 2001),
b) 89-25A (IDAC 110401-1, deposited Apr. 11, 2001),
c) 94-26 (IDAC 230201-2, deposited Feb. 23, 2001),
d) 94-44B (IDAC 230201-3, deposited Feb. 23, 2001)
e) 94-134 (IDAC 230201-4, deposited Feb. 23, 2001),
f) 94-359A (IDAC 110401-2, deposited Apr. 11, 2001),
g) 95-54A1 (IDAC 230201-5, deposited Feb. 23, 2001),
h) 95-268B (IDAC 110401-3, deposited Apr. 11, 2001),
i) 97-12B (IDAC 230201-6, deposited Feb. 23, 2001), and
j) 97-15B2 (IDAC 110401-4, deposited Apr. 11, 2001).

33. The method of claim 7, wherein said crop is a perennial crop.

34. The method of claim 33, wherein said perennial crop is selected from the group consisting of a turf, a perennial grass, and a winter cereal.

35. The method of claim 8, wherein said crop is a perennial crop.

36. The method of claim 35, wherein said perennial crop is selected from the group consisting of a turf, a perennial grass, and a winter cereal.

37. The method of claim 9, wherein said crop is a perennial crop.

38. The method of claim 37, wherein said perennial crop is selected from the group consisting of a turf, a perennial grass, and a winter cereal.

39. The method of claim 10, wherein said crop is a perennial crop.

40. The method of claim 39, wherein said perennial crop is selected from the group consisting of a turf, a perennial grass, and a winter cereal.

41. The method of claim 11, wherein said crop is a perennial crop.

42. The method of claim 41, wherein said perennial crop is selected from the group consisting of a turf, a perennial grass, and a winter cereal.

43. The method of claim 12, wherein said crop is a perennial crop.

44. The method of claim 43, wherein said perennial crop is selected from the group consisting of a turf, a perennial grass, and a winter cereal.

45. The method of claim 13, wherein said crop is a perennial crop.

46. The method of claim 45, wherein said perennial crop is selected from the group consisting of a turf, a perennial grass, and a winter cereal.

47. The method of claim 14, wherein said crop is a perennial crop.

48. The method of claim 47, wherein said perennial crop is selected from the group consisting of a turf, a perennial grass, and a winter cereal.

49. A method of controlling weed development during growth of a lawn of grass, the method comprising:

a) adding an effective amount of said biocontrol agent of claim 4 to produce a treated soil, b) planting grass seed in said treated soil, c) growing said lawn from said grass seed.

50. A method of controlling weed development during growth of a lawn of grass, the method comprising:

a) planting grass seed, b) adding an effective amount of said biocontrol agent of claim 4 to soil where said grass seed is planted, c) growing said lawn from said grass seed.

51. A method of controlling weed development during growth of a lawn of grass comprising:

a) adding an effective amount of a biocontrol agent of claim 4 to grass seed to produce treated grass seed;

b) planting said treated grass seed; and c) growing said lawn from said treated grass seed.

52. A method of controlling weed development during growth of an established lawn of grass, the method comprising:

a) adding an effective amount of the biocontrol agent of claim 4 to the established lawn; and b) growing the lawn.

53. A method of controlling weed development during growth of a lawn of grass, the method comprising:

a) adding an effective amount of said biocontrol composition of claim 5 to produce a treated soil, b) planting grass seed in said treated soil, c) growing said lawn from said grass seed.

54. A method of controlling weed development during growth of a lawn of grass, the method comprising:

a) planting grass seed, b) adding an effective amount of said biocontrol composition of claim 5 to soil where said grass seed is planted, c) growing said lawn from said grass seed.

55. A method of controlling weed development during crop growth comprising:

a) adding an effective amount of a biocontrol composition of claim 5 to grass seed to produce treated grass seed;

b) planting said treated grass seed; and c) growing a lawn from said treated grass seed.

56. A method of controlling weed development during growth of an established lawn, the method comprising:

a) adding an effective amount of the biocontrol composition of claim 5 to the established lawn; and b) growing the lawn.

57. The method of claim 16, wherein said biocontrol agent is applied to the soil before emergence of the weed.

58. The method of claim 16, wherein said biocontrol agent is applied to the soil after emergence of the weed.

59. The method of claim 18, wherein said biocontrol composition is applied to the soil before emergence of the weed.

60. The method of claim 18, wherein said biocontrol composition is applied to the soil after emergence of the weed.

61. A method of enhancing the growth of a crop, the method comprising:

a) adding an effective amount of the biocontrol agent of claim 4 to soil to produce a treated soil;

b) planting crop seed in said treated soil, and c) growing said crop from the crop seed.

62. A method of enhancing the growth of a crop, the method comprising:

a) planting crop seed in soil;

b) adding an effective amount of the biocontrol agent of claim 4 to the soil where said crop seed is planted, and c) growing said crop from the crop seed.

63. A method of enhancing the growth of an established crop, the method comprising:

a) adding an effective amount of the biocontrol agent of claim 4 to the established crop;

and b) growing the crop.

64. A method of enhancing the growth of a crop, the method comprising:

a) adding an effective amount of said biocontrol agent of claim 4 to a crop seed to produce a treated crop seed;

b) planting said treated crop seed; and c) growing said crop.

65. The method of claim 61, wherein said crop is a grass.

66. The method of claim 62, wherein said crop is a grass.

67. The method of claim 63, wherein said crop is a grass.

68. The method of claim 64, wherein said crop is a grass, and said crop seed is grass seed.

69. The biocontrol agent of claim 4, wherein said one or more than one *Phoma* isolate is selected from the group consisting of a) 85-24B (IDAC 230201-1, deposited Feb. 23, 2001), b) 89-25A (IDAC 110401-1, deposited Apr. 11, 2001), c) 94-26(IDAC 230201-2, deposited Feb. 23, 2001)

d) 94-44B (IDAC 230201-3, deposited Feb. 23, 2001)

e) 94-134(IDAC 230201-4, deposited Feb. 23, 2001), f) 94-359A (IDAC 110401-2, deposited Apr. 11, 2001), g) 95-54A1(IDAC 230201-5, deposited Feb. 23, 2001), h) 95-268B (IDAC 110401-3, deposited Apr. 11, 2001), i) 97-12B (IDAC 230201-6, deposited Feb. 23, 2001), j) 97-15B2(IDAC 110401-4, deposited Apr. 11, 2001), and a combination thereof.

* * * * *